US011166605B2

(12) United States Patent
Kirschman

(10) Patent No.: US 11,166,605 B2
(45) Date of Patent: Nov. 9, 2021

(54) SANITARY FORCED-AIR HAND DRYER

(71) Applicant: David Louis Kirschman, Dayton, OH (US)

(72) Inventor: David Louis Kirschman, Dayton, OH (US)

(73) Assignee: THUNDERHILL INVESTMENTS, LLC, Dayton, OH (US)

( * ) Notice: Subject to any disclaimer, the term of this patent is extended or adjusted under 35 U.S.C. 154(b) by 0 days.

(21) Appl. No.: 16/854,028

(22) Filed: Apr. 21, 2020

(65) Prior Publication Data

US 2020/0245826 A1  Aug. 6, 2020

Related U.S. Application Data

(63) Continuation of application No. 16/149,378, filed on Oct. 2, 2018, now Pat. No. 10,722,083.

(60) Provisional application No. 62/567,356, filed on Oct. 3, 2017.

(51) Int. Cl.
*A47K 10/48* (2006.01)
*A61L 9/20* (2006.01)

(52) U.S. Cl.
CPC .............. *A47K 10/48* (2013.01); *A61L 9/20* (2013.01); *A61L 2209/111* (2013.01); *A61L 2209/12* (2013.01); *A61L 2209/14* (2013.01)

(58) Field of Classification Search
CPC ..... A47K 10/49; A61L 9/20; A61L 2209/111; A61L 2209/12; A61L 2209/14; A61L 2/0047; A61L 27/3691; A61L 2/26; F26B 21/004

USPC ............................................................. 34/82
See application file for complete search history.

(56) References Cited

U.S. PATENT DOCUMENTS

| | | | | |
|---|---|---|---|---|
| 3,766,397 A | ‡ | 10/1973 | Rockson ................. | A47K 10/48 250/43 |
| 4,087,925 A | ‡ | 5/1978 | Bienek .................... | A47K 10/48 250/43 |
| 4,383,377 A | ‡ | 5/1983 | Crafton ................... | A47K 10/48 239/13 |
| 4,625,119 A | ‡ | 11/1986 | Murdock, III ........... | A47K 1/09 250/45 |
| 5,459,944 A | ‡ | 10/1995 | Tatsutani ................ | A47K 10/48 34/202 |
| 6,185,838 B1 | ‡ | 2/2001 | Moore .................... | A47K 10/48 34/202 |

(Continued)

FOREIGN PATENT DOCUMENTS

| | | |
|---|---|---|
| EP | 1908384 | 4/2008 |
| EP | 1908384 A1 | 4/2008 |

(Continued)

*Primary Examiner* — Stephen M Gravini
(74) *Attorney, Agent, or Firm* — Jacox, Meckstroth & Jenkins

(57) ABSTRACT

A forced-air hand dryer having means and apparatus for decontaminating air passing through the forced-air hand dryer. In general, the embodiments described comprise at least one or a plurality of airflow generators, at least one conduit for passing air through the conduits and to at least one decontamination system where the air undergoes filtration and decontamination. The air generated may be located upstream or downstream of a hand-receiving area where a user places his or her hands for drying.

42 Claims, 16 Drawing Sheets

(56) References Cited

U.S. PATENT DOCUMENTS

| | | | | |
|---|---|---|---|---|
| 6,497,840 | B1 * | 12/2002 | Palestro | A61L 9/20 250/432 R |
| 6,576,188 | B1 * | 6/2003 | Rose | A61L 2/02 422/121 |
| 7,039,301 | B1 ‡ | 5/2006 | Aisenberg | A47K 10/48 34/201 |
| 7,856,736 | B2 ‡ | 12/2010 | Churchill | A47K 10/48 34/202 |
| 7,946,055 | B2 ‡ | 5/2011 | Churchill | A47K 10/48 134/26 |
| 7,971,368 | B2 | 7/2011 | Fukaya et al. | |
| 8,155,508 | B2 ‡ | 4/2012 | Caine | A47K 10/48 34/267 |
| 8,341,853 | B2 ‡ | 1/2013 | French | A47K 10/48 15/300 |
| 8,347,521 | B2 ‡ | 1/2013 | Churchill | A47K 10/48 134/26 |
| 8,347,522 | B2 ‡ | 1/2013 | Dyson | A47K 10/48 34/90 |
| 8,490,291 | B2 ‡ | 7/2013 | Churchill | A47K 10/48 222/1 |
| 8,607,472 | B2 * | 12/2013 | Ishii | A61L 2/24 34/526 |
| 9,057,560 | B2 ‡ | 6/2015 | Dyson | F26B 21/004 |
| 9,060,657 | B2 ‡ | 6/2015 | Ryan | A47K 10/48 |
| 9,308,289 | B2 ‡ | 4/2016 | Graff | A61L 9/20 |
| 9,441,885 | B2 * | 9/2016 | Bayley | A47K 4/00 |
| 9,457,119 | B2 | 10/2016 | Kirschman | |
| 9,538,886 | B2 | 1/2017 | Ros Marin | |
| 9,565,979 | B2 | 2/2017 | Maclaine et al. | |
| 9,642,505 | B2 ‡ | 5/2017 | Bayley | E03C 1/01 |
| 9,743,813 | B2 ‡ | 8/2017 | Courtney | A47K 10/48 |
| 9,743,814 | B2 ‡ | 8/2017 | Ryan | F26B 25/06 |
| 9,746,237 | B2 ‡ | 8/2017 | Smith | A47K 10/48 |
| 9,826,865 | B2 | 11/2017 | Maruyama et al. | |
| 10,349,792 | B2 | 7/2019 | Homma et al. | |
| 10,362,910 | B2 | 7/2019 | Chou | |
| 10,455,992 | B2 * | 10/2019 | Satermo | B64D 11/02 |
| 10,532,122 | B2 | 1/2020 | Kirschman | |
| 10,722,083 | B2 * | 7/2020 | Kirschman | A61L 9/20 |
| 10,874,266 | B2 * | 12/2020 | Childress | A47K 10/48 |
| 2003/0217641 | A1 ‡ | 11/2003 | Palestro | A61L 9/20 95/273 |
| 2006/0272170 | A1 ‡ | 12/2006 | Holmes | A61L 9/20 34/275 |
| 2008/0253754 | A1 ‡ | 10/2008 | Rubin | A47K 10/48 392/38 |
| 2009/0119942 | A1 ‡ | 5/2009 | Aisenberg | A47K 10/48 34/418 |
| 2011/0023319 | A1 ‡ | 2/2011 | Fukaya | A47K 10/48 34/202 |
| 2011/0277342 | A1 ‡ | 11/2011 | Ishii | A47K 10/48 34/526 |
| 2012/0285033 | A1 ‡ | 11/2012 | Hsu | A47K 10/48 34/202 |
| 2012/0291303 | A1 ‡ | 11/2012 | Courtney | A47K 10/48 34/202 |
| 2013/0031799 | A1 ‡ | 2/2013 | Gagnon | A47K 10/48 34/526 |
| 2015/0328355 | A1 | 11/2015 | Rubin | |
| 2019/0099050 | A1 | 4/2019 | Kirschman | |
| 2020/0245826 | A1 * | 8/2020 | Kirschman | A47K 10/48 |

FOREIGN PATENT DOCUMENTS

| | | | |
|---|---|---|---|
| EP | 3290057 | 3/2018 | |
| EP | 3290057 A1 | 3/2018 | |
| KR | 101416877 B1 * | 7/2014 | B01D 46/10 |
| KR | 100909730 | 3/2018 | |
| WO | WO-2005074776 A1 * | 8/2005 | A47K 10/48 |
| WO | 2006058370 A1 | 6/2006 | |
| WO | WO 2006058370 | 6/2006 | |
| WO | 2007013142 A1 | 2/2009 | |
| WO | WO 2007013142 | 2/2009 | |
| WO | WO-2013100352 A1 * | 7/2013 | B01D 46/10 |
| WO | 2013149285 A1 | 10/2013 | |
| WO | WO 2013149285 | 10/2013 | |

\* cited by examiner
‡ imported from a related application

FIG. 8A
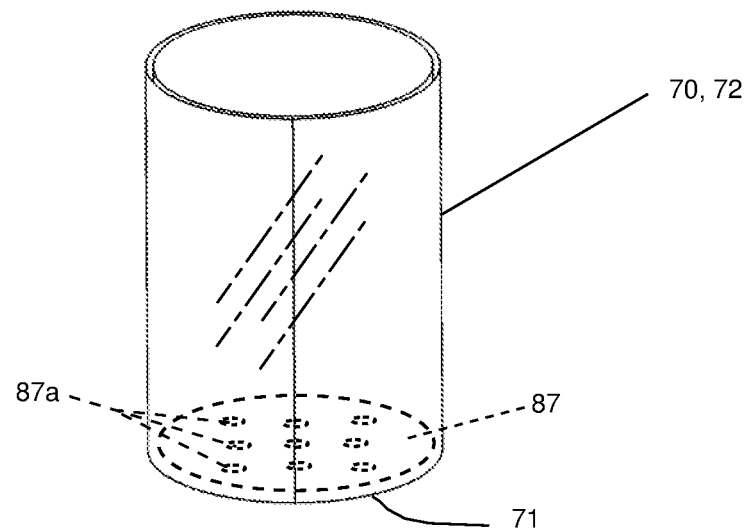
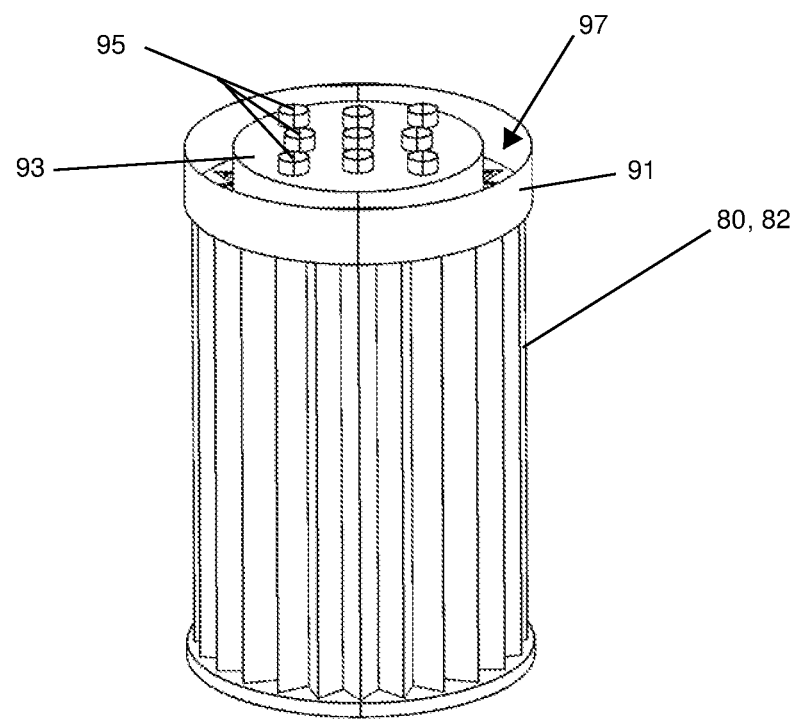

SANITARY FORCED-AIR HAND DRYER

CROSS-REFERENCE TO RELATED APPLICATION

The present application is a continuation of U.S. application Ser. No. 16/149,378 filed Oct. 2, 2019, which claims priority to provisional U.S. Application Ser. No. 62/567,356, filed Oct. 3, 2017, to which Applicant claims the benefit of the earlier filing date. These applications are incorporated herein by reference and made a part hereof.

BACKGROUND OF THE INVENTION

1. Field of the Invention

This invention relates to a forced-air hand dryer and, more particularly, to a forced-air hand dryer having means and apparatus for decontaminating air passing through the forced-air hand dryer.

2. Description of the Related Art

Forced-air hand dryers are increasingly used due to their low environmental impact and cost of operation compared to other hand-drying methods, such as paper towels. However, a significant drawback of forced-air hand dryers is the potential for environmental contamination. Forced-air hand dryers can spread contaminated bioaerosols onto the user, environmental air and surfaces. This is especially important in healthcare and food-service areas, where the spread of infectious pathogens can have detrimental effects on human health.

What is needed, therefore, is an improved forced-air hand dryer which has less environmental impact.

SUMMARY OF THE INVENTION

It is, therefore, a primary object of the invention to provide a decontamination system for use with a hand dryer.

Another object of one embodiment of the invention is to provide a decontamination system that decontaminates waste air from the hand dryer before it is exhausted or returned to an environment.

Another object of one embodiment of the invention is to provide a forced-air hand dryer that uses negative pressure at a hand-receiving area where a user places his or her hands.

Still another object of one embodiment of the invention is to provide a forced-air hand dryer wherein at least one or a plurality of airflow generators are situated upstream of the hand-receiving area.

Yet another object of one embodiment of the invention is to provide an embodiment wherein the airflow generators are located downstream of the hand-receiving area and generate a negative pressure at the hand-receiving area.

Still another object of one embodiment of the invention is to provide a forced-air hand dryer that uses a positive pressure at the hand-receiving area and that has a decontamination system located downstream of the hand-receiving area in order to capture and decontaminate waste air from the hand-receiving area.

Still another object of one embodiment of the invention is to provide a hand dryer that may be used in a hospital environment, a lavatory or bathroom environment, a kitchen or cooking environment, school, public restrooms, a surgical room or hospital environment, elderly home, or other healthcare of food-service environments.

In the first embodiment of the invention, the hands are placed in the vicinity of a negative pressure air intake, such that aerosols are directly drawn into the device, rather than the environment. The negative pressure is created by a Venturi effect where a high velocity air column of decreasing diameter is used to create the required negative air movement over the hands. In the second embodiment of the current invention, positive pressure air is directed onto user hands and waste air and aerosols ejected from user hands is collected in a separate negative pressure collector, preventing aerosols from entering the surrounding environment. In the third embodiment, negative pressure is directly created by vacuum fans operating at the waste air collector. In each embodiment, waste air and contaminants are filtered using means such as high efficiency particulate air (HEPA) filtration and/or ultraviolet decontamination.

In one aspect, one embodiment of the invention comprises a hand dryer comprising at least one airflow generator for generating an airflow for the hand dryer; at least one decontamination system; at least one conduit for defining at least one passageway for fluidly coupling the at least one airflow generator to at least one anti-bacterial treatment system so that air can flow therebetween; at least one hand-receiving opening that is in fluid communication with the at least one passageway and dimensioned to receive at least one hand of a person; the at least one airflow generator generating the airflow that causes a drying airflow across the at least one hand of the person to facilitate drying the at least one hand after it has been positioned in the at least one hand-receiving opening; the at least one anti-bacterial treatment system being situated downstream of the at least one hand-receiving opening so that at least a portion of the drying airflow or the airflow is channeled by the at least one conduit to the at least one decontamination system so that at least a portion of the drying airflow or the airflow is filtered or treated to facilitate reducing contamination.

In another aspect, one embodiment of the invention comprises a hand dryer comprising at least one airflow generator for generating an airflow for drying a user's hands; a hand-drying area operatively associated with the at least one airflow generator for defining a place for the user to place their hands; and a decontamination system downstream of the hand-drying area for receiving waste airflow after it passes the user's hands; the at least one airflow generator generating a positive airflow over the user's hands to facilitate drying them and the decontamination system receiving the waste airflow and decontaminating the waste airflow after it has passed over the user's hands.

In yet another aspect, one embodiment of the invention comprises a hand dryer comprising at least one airflow generator for generating an airflow; a hand-receiving area defining at least one hand-receiving opening for a user to place their hands; and at least one decontamination system downstream of the hand-receiving area; the at least one airflow generator generating a negative pressure at the hand-receiving area to cause a drying airflow across the hands of the user to facilitate drying the hands after they have been positioned in the at least one hand-receiving opening.

In still another aspect, one embodiment of the invention comprises a forced-air hand dryer comprising a means for creating a positive air flow; a Venturi chamber for generating negative air pressure from the positive air flow, the negative air pressure creating a negative air flow from the atmosphere into the chamber; and an air inlet to direct the negative air flow over hands; the negative air flow combining with dryer waste air into an air collection means; the air collection means comprising a decontamination means purposed to decontaminate the waste air.

In still another aspect, one embodiment of the invention comprises a forced-air hand dryer comprising a means for creating a positive air flow; an air output transmitting the positive air flow upon hands; an air input means purposed to receive waste air from the hands; and an air decontamination means purposed to decontaminate the waste air.

In still another aspect, one embodiment of the invention comprises a forced-air hand dryer comprising a means for creating a negative air pressure; an air input means to utilize the negative air pressure to create an air flow over hands, the air input further comprising a means to collect waste air from hands; and an air decontamination means purposed to decontaminate the waste air.

This invention, including all embodiments shown and described herein, could be used alone or together and/or in combination with one or more of the features covered by one or more of the following list of features:

The hand dryer wherein the drying airflow is caused by a negative pressure at the at least one hand-receiving opening.

The hand dryer wherein the drying airflow is caused by a positive pressure at the at least one hand-receiving opening.

The hand dryer wherein the at least one conduit comprises at least one tubular member that defines a high velocity air column dimensioned and sized to create a negative pressure at the at least one hand-receiving opening The hand dryer wherein the at least one tubular member comprises a generally decreasing dimension in order to create a Venturi effect and to create a negative pressure at the at least one hand-receiving opening.

The hand dryer wherein the tubular member is dimensioned to create a Venturi effect that causes a negative pressure at the at least one hand-receiving opening.

The hand dryer wherein the at least one decontamination system comprises at least one physical, biological or emissive means for removing, capturing and/or inactivating organic, inorganic or living matter from at least one of the airflow or the drying airflow.

The hand dryer wherein the at least one decontamination system comprises at least one of an air filter or ultraviolet light source for generating ultraviolet light for decontaminating the air received by the at least one decontamination system.

The hand dryer wherein the hand dryer comprises a plurality of conduits defining a plurality of passageways, respectively, for directing airflow from the at least one airflow generator to the at least one decontamination system.

The hand dryer wherein the hand dryer comprises a plurality of hand-receiving openings in fluid communication with the plurality of passageways, each of the plurality of hand-receiving openings being situated adjacent each other so that the person may situate at least one hand in each of the plurality of hand-receiving openings.

The hand dryer wherein each of the plurality of hand-receiving openings are defined by at least one wall having a plurality of perforations therein for facilitating creation of the drying airflow.

The hand dryer wherein the hand dryer comprises a plurality of fans for creating an airflow in each of the plurality of conduits, respectively.

The hand dryer wherein the at least one decontamination system comprises at least one filter or ultraviolet light source associated with an outlet end of each of the plurality of conduits.

The hand dryer wherein the at least one airflow generator is a fan.

The hand dryer wherein the drying airflow is caused by a negative pressure at the at least one hand-opening.

The hand dryer wherein the decontamination system comprises an input, the input having at least a portion that defines a surface for channeling or funneling air into the decontamination system.

The hand dryer wherein the at least one airflow generator comprises an outlet and the decontamination system comprises an inlet, the outlet and inlet being spaced from each other and the hand-drying area being situated between the outlet and the inlet; the outlet having a predetermined configuration adapted to direct airflow from the at least one airflow generator to the hand-drying area and the inlet of the decontamination system having a predetermined configuration that facilitates channeling or funneling air into the decontamination system after it has passed the user's hands.

The hand dryer wherein the drying airflow is caused by a positive pressure at the hand-drying area.

The hand dryer wherein the decontamination system comprises at least one physical, biological or emissive means for removing, capturing and/or inactivating organic, inorganic or living matter from at least one of the airflow or the drying airflow.

The hand dryer wherein the decontamination system comprises at least one of either an air filter or an ultraviolet light source for generating ultraviolet light for decontaminating the air received by the decontamination system.

The hand dryer wherein the decontamination system comprises at least one filter or ultraviolet light source downstream of an inlet to the decontamination system.

The hand dryer wherein the at least one airflow generator is at least one radial fan.

The hand dryer wherein the at least one airflow generator generates a positive pressure drying airflow at the hand-drying area.

The hand dryer wherein the decontamination system comprises a negative pressure collector for generating a negative pressure relative to the hand-drying area to facilitate preventing aerosols or the waste air from entering a surrounding environment.

The hand dryer wherein the negative pressure collector comprises a vacuum generator for generating the negative pressure at an inlet of the decontamination system.

The hand dryer wherein the at least one decontamination system defining at least one anti-bacterial treatment system so that after the airflow passes the user's hands, at least a portion of the airflow is received or channeled into the at least one decontamination system as a result of the negative pressure generated by the at least one airflow generator so that at least a portion of the airflow is filtered or treated to facilitate reducing contamination.

The hand dryer wherein the at least one airflow generator is located downstream of the hand-receiving area.

The hand dryer wherein the at least one airflow generator is located in the decontamination system.

The hand dryer wherein the drying airflow is caused by a negative pressure at the hand-receiving area.

The hand dryer wherein the hand dryer comprises at least one conduit for receiving and channeling ambient air toward the hand-receiving area, the at least one conduit comprising at least one hand enclosure, respectively, for receiving at least one hand of the user.

The hand dryer wherein the at least one hand enclosure is perforated to permit ambient air to enter into the hand-receiving area.

The hand dryer wherein the hand dryer comprises a plurality of hand-receiving openings in fluid communication with the plurality of passageways, each of the plurality of hand-receiving openings being situated adjacent each other so that the user may situate at least one hand in each of the plurality of hand-receiving openings, respectively.

The hand dryer wherein each of the plurality of hand-receiving openings are defined by at least one wall having a plurality of perforations therein for facilitating creation of the drying airflow.

The hand dryer wherein the hand dryer comprises a plurality of fans situated in the at least one decontamination system for creating a negative air pressure at the hand-receiving area.

The hand dryer wherein the at least one decontamination system comprises at least one of either a filter or an ultraviolet light source associated with an outlet end of each of the plurality of conduits.

The hand dryer wherein the at least one airflow generator is a fan associated with the at least one decontamination system.

The forced-air hand dryer wherein the means for creating a positive air flow is a fan.

The forced-air hand dryer wherein the air inlet comprises at least one partially open chamber dimensioned to receive hands.

The forced-air hand dryer wherein the decontamination means comprises physical, biological or emissive means for removing, capturing and/or inactivating organic, inorganic or living matter.

The forced-air hand dryer wherein the air input means comprises a complete or partial funnel.

The forced-air hand dryer wherein the means for creating a negative air pressure is a fan.

The forced-air hand dryer wherein the means for creating a negative air pressure incorporates a low pressure chamber.

The forced-air hand dryer wherein the means to collect waste air incorporates a low pressure chamber.

The forced-air hand dryer wherein the air input means comprises a means for increasing air velocity, such as a partially open chamber in proximity to the hands.

These and other objects and advantages of the invention will be apparent from the following description, the accompanying drawings and the appended claims.

BRIEF DESCRIPTION OF THE ACCOMPANYING DRAWINGS

FIG. 8A is a view showing a transparent tubular member and an associated filter;

DETAILED DESCRIPTION OF THE PREFERRED EMBODIMENTS

Figure 1:
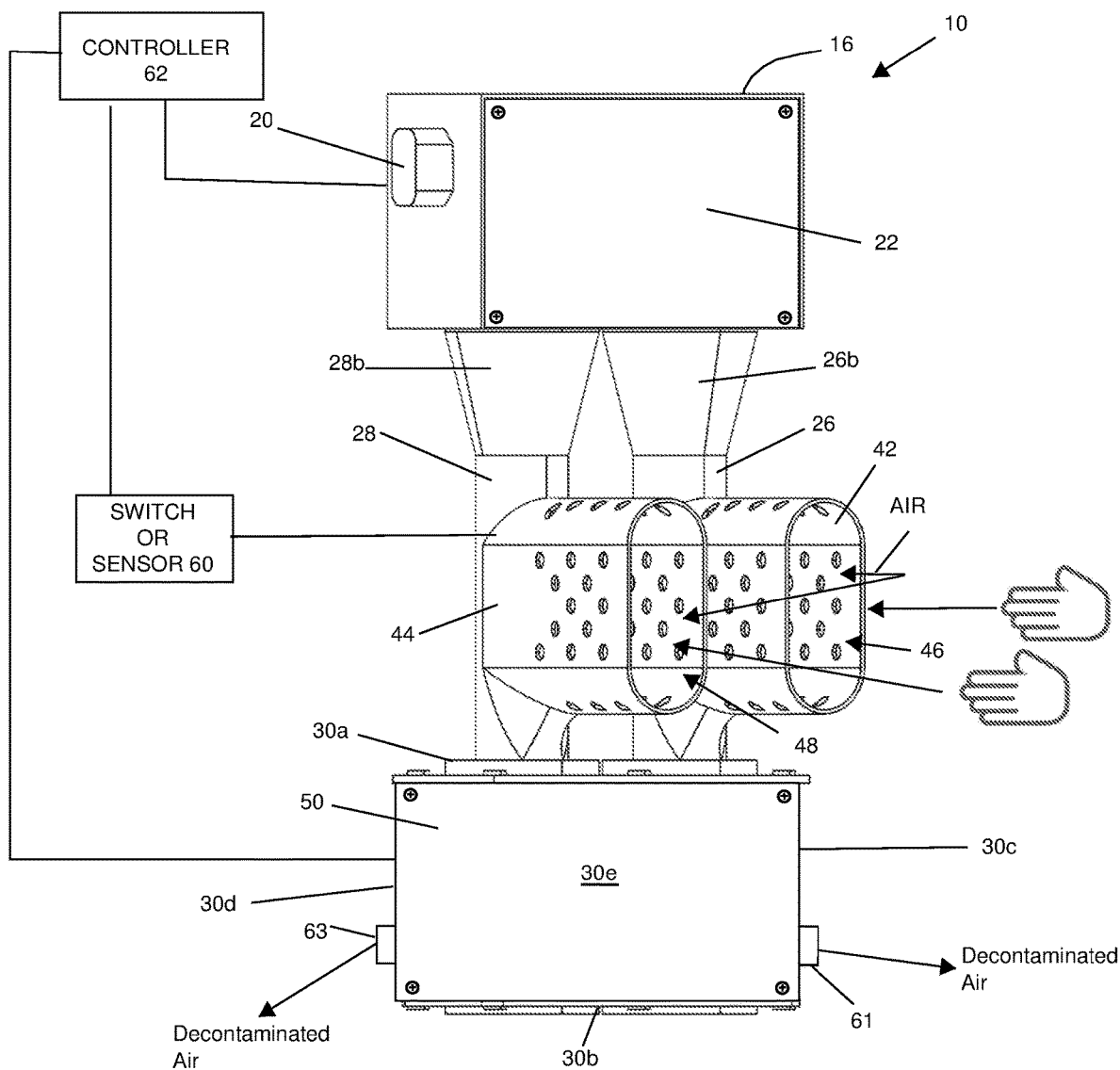
FIG. 1 is a perspective view of a first embodiment of a forced-air hand dryer.
Figure 2:
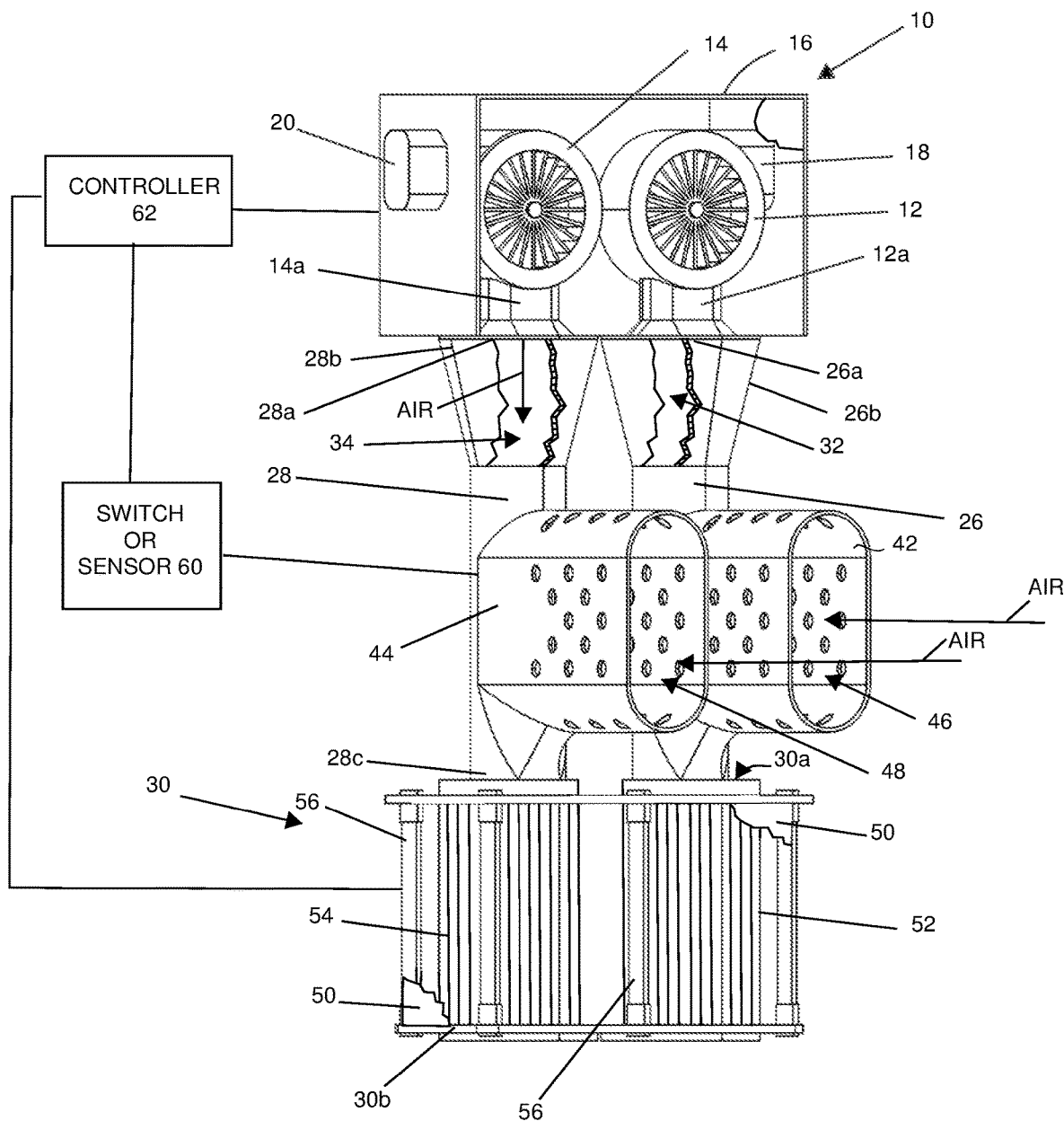
FIG. 2 is a perspective view similar to FIG. 1 showing a panel of the airflow generators being removed and showing the housing of the decontamination system also being fragmented away.

Referring now to FIGS. 1-5, a first embodiment of a forced-air hand dryer 10 is shown. In this embodiment, the forced-air hand dryer 10 comprises means for creating a positive airflow. In the illustration being described, the means include at least one or a plurality of airflow generators 12 and 14 for generating airflow. The airflow generators 12 and 14 are housed in a housing 16 having a first inlet or duct 18 for introducing air to the first airflow generator 12 and a second inlet or duct 20 for introducing air to the second airflow generator 14. In the illustration being described, the airflow generators 12 and 14 are housed in the housing 16 that surrounds and encapsulates the airflow generators 12 and 14. In the illustration, a front cover 22 of the housing is adapted to be removed for service.

In the illustration being described, the forced airflow from the plurality of airflow generators 12 and 14 causes a negative air pressure in at least one or a plurality of hand-receiving openings 46 and 48 (described later herein). Note that each of the airflow generators 12 and 14 comprises an outlet 12a and 14a, respectively, which is coupled to an inlet 26a and 28a of a first conduit 26 and a second conduit 28, respectively. It is important to note that the plurality of conduits 26 and 28 are generally tubular and each define a conduit or passageway 32 and 34 (FIG. 2), respectively, through which air may flow from the first and second airflow generators 12 and 14, respectively. For ease of illustration, the first conduit 26 and second conduit 28 are shown fragmented in FIG. 2 in order to illustrate the airflow. It is important to note that each of the plurality of conduits 26 and 28 define at least on passageway for fluidly coupling the airflow generators 12 and 14 to a decontamination system comprising at least one anti-bacterial treatment system 30, which will be described in more detail later herein.

Each of the conduits 26 and 28 define the passageways 32 and 34, respectively, for directing airflow from the first and second airflow generators 12 and 14, respectively, to the at least one anti-bacterial treatment system 30, as mentioned.

Each of the first and second conduits 26 and 28 comprise at least one or a plurality of hand-receiving walls 42 and 44, respectively, that define a first hand-receiving opening 46 and a second hand-receiving opening 48, respectively. The first and second hand-receiving openings 46 and 48 are in fluid communication with passageways 32 and 34. The fragmentary view of FIG. 3 illustrates the fluid communication of passageway 34 and hand-receiving opening 48, with the passageway 32 and hand-receiving opening 48 similarly constructed and in fluid communication.

Figure 3:
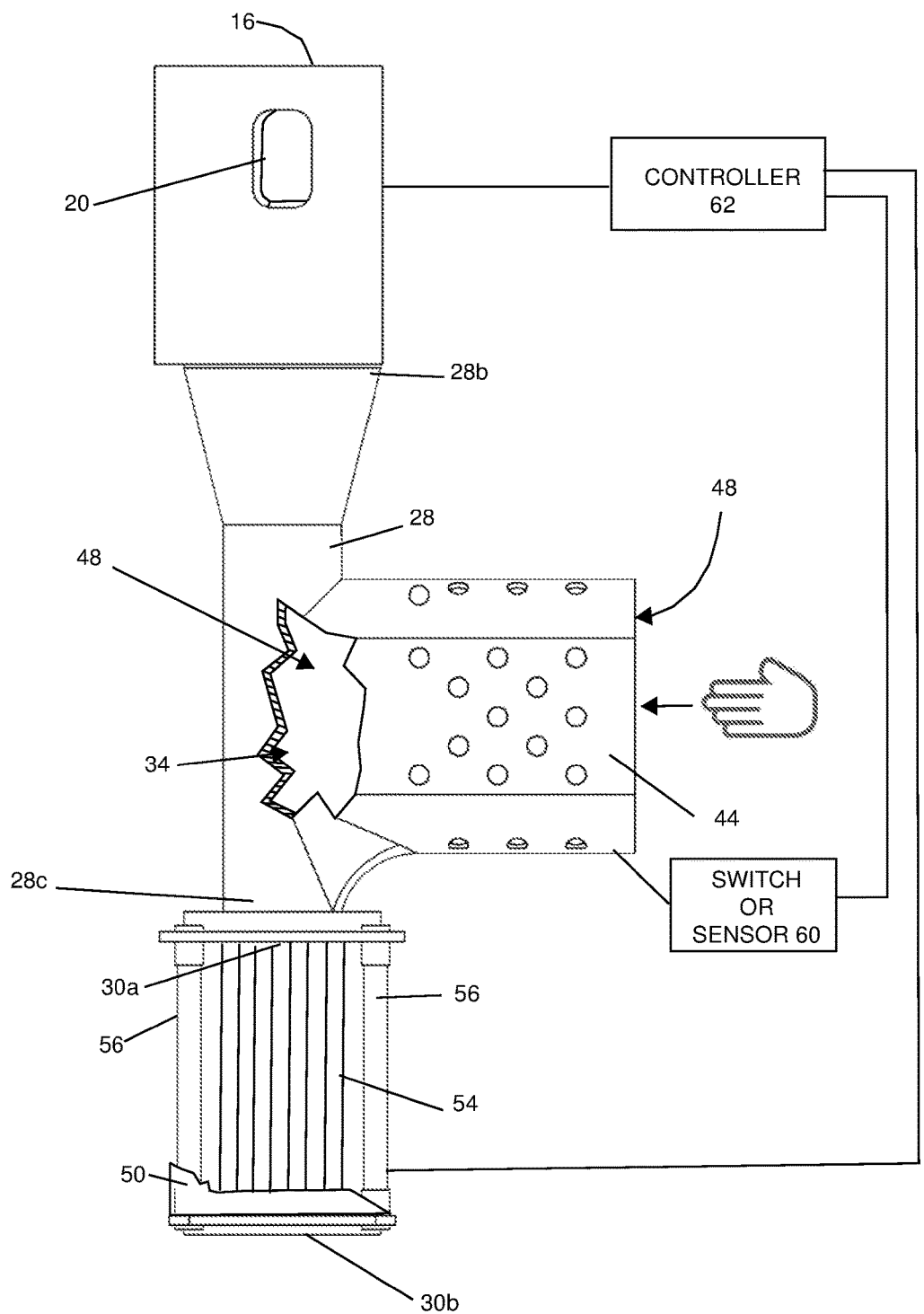
FIG. 3 is a partial fragmentary view showing the fluid communication between a hand-receiving area and the conduit with which it is associated.
Figure 4:
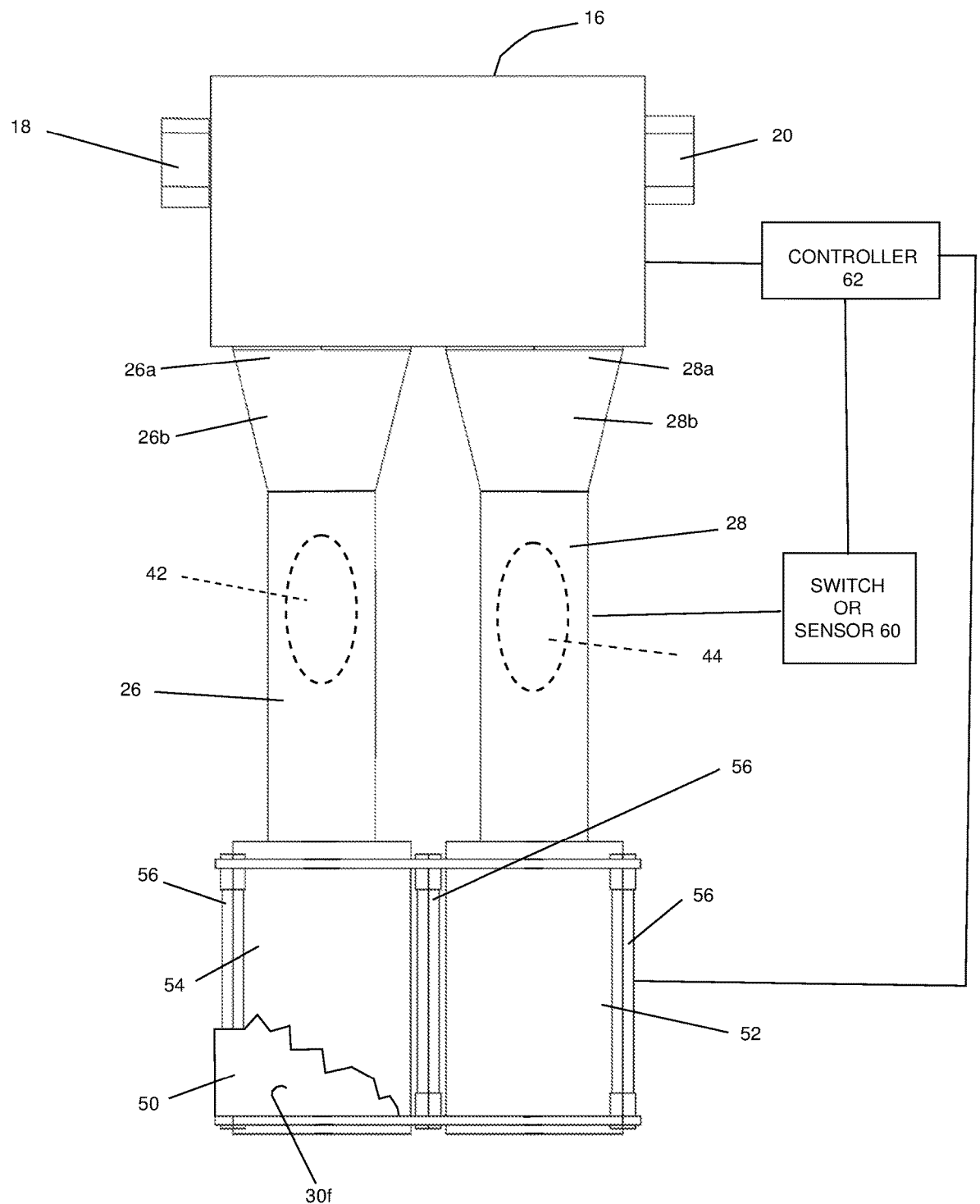
FIG. 4 is a fragmentary rear view of the embodiment shown in FIG. 1.
Figure 5:
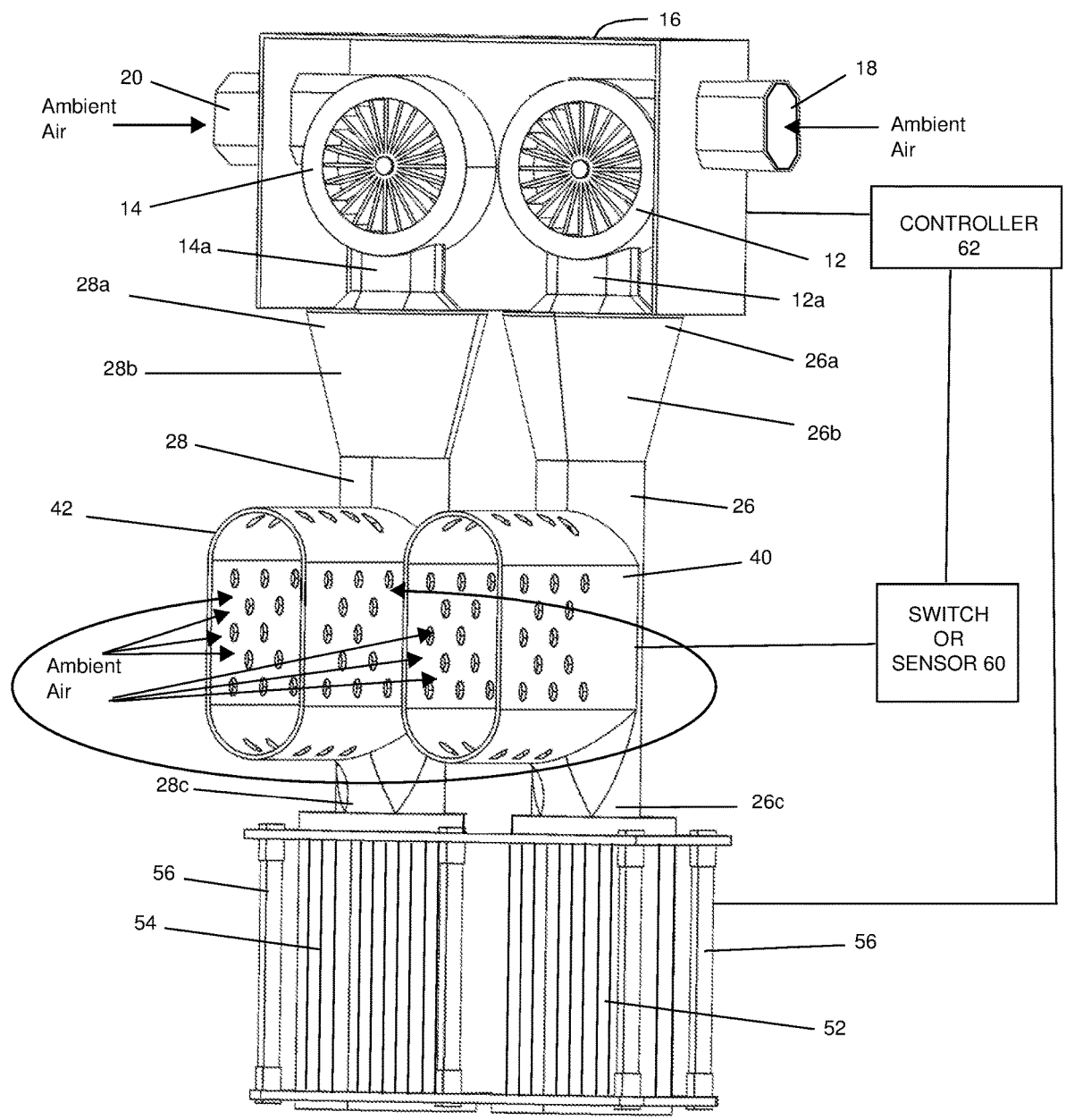
FIG. 5 is another perspective view similar to the view of FIG. 2 illustrating further details of the first embodiment.
Figure 6:
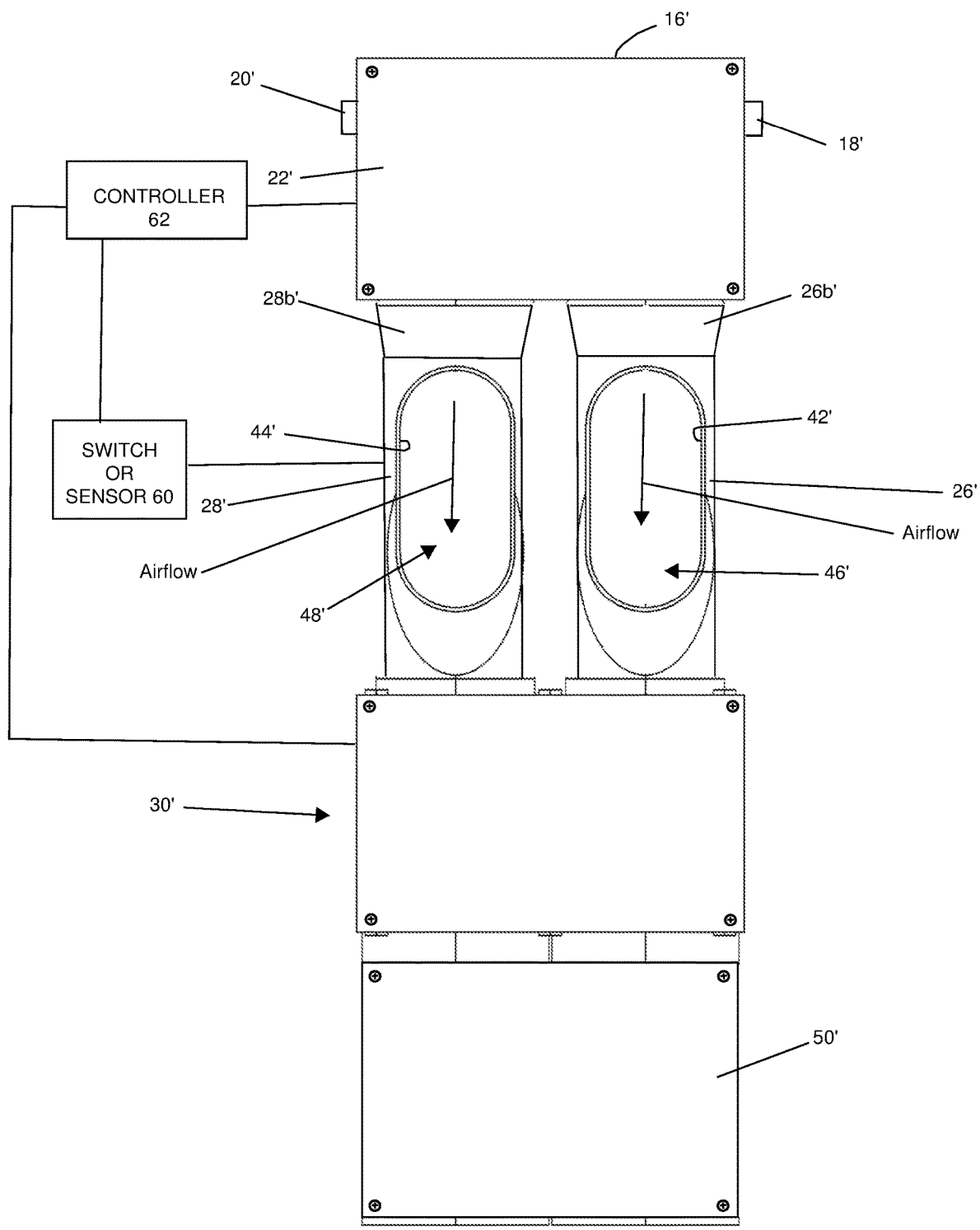
FIG. 6 is a view of a second embodiment of a forced-air hand dryer.
Figure 7:
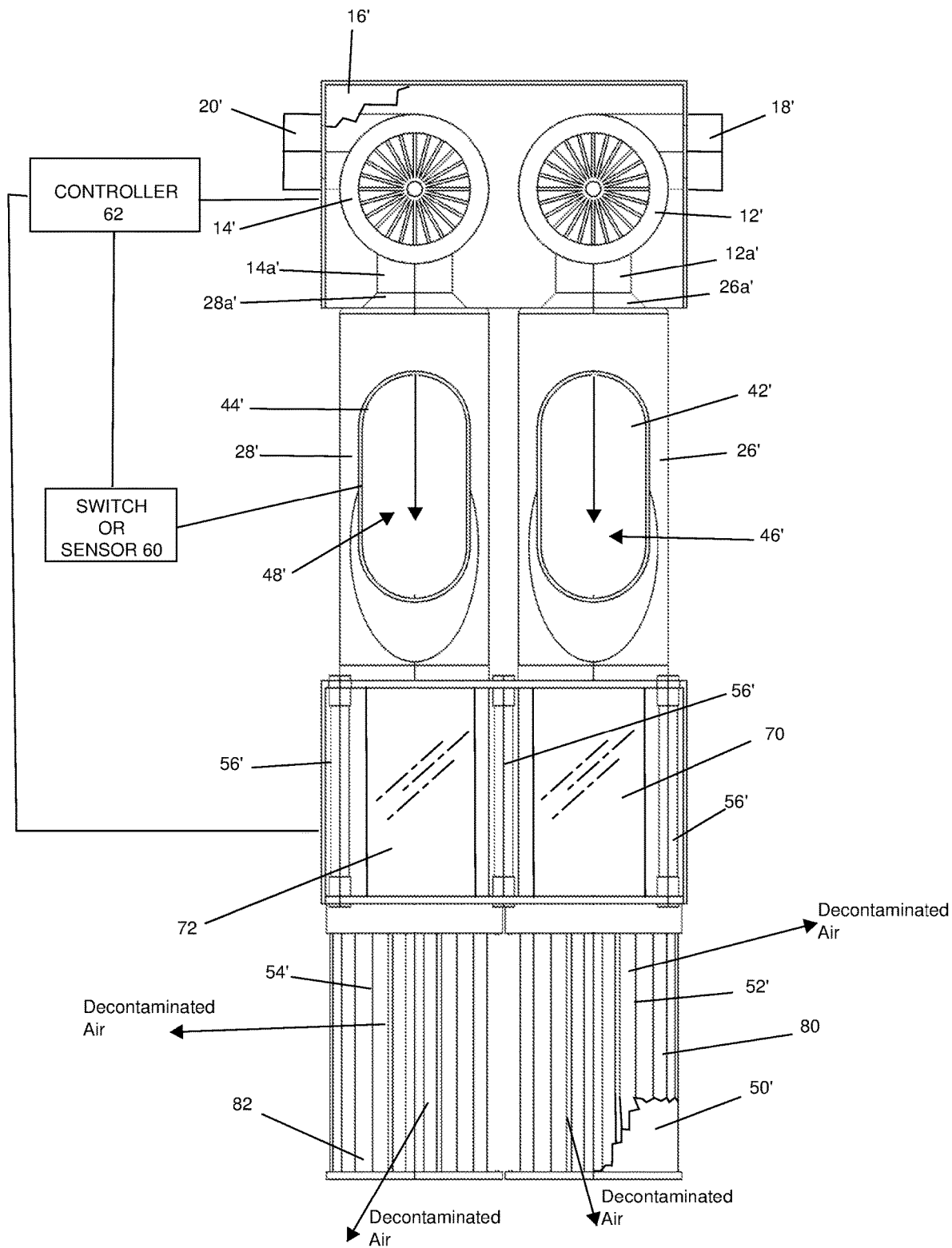
FIG. 7 is a plan view of the forced-air hand dryer shown in FIG. 6.
Figure 8:
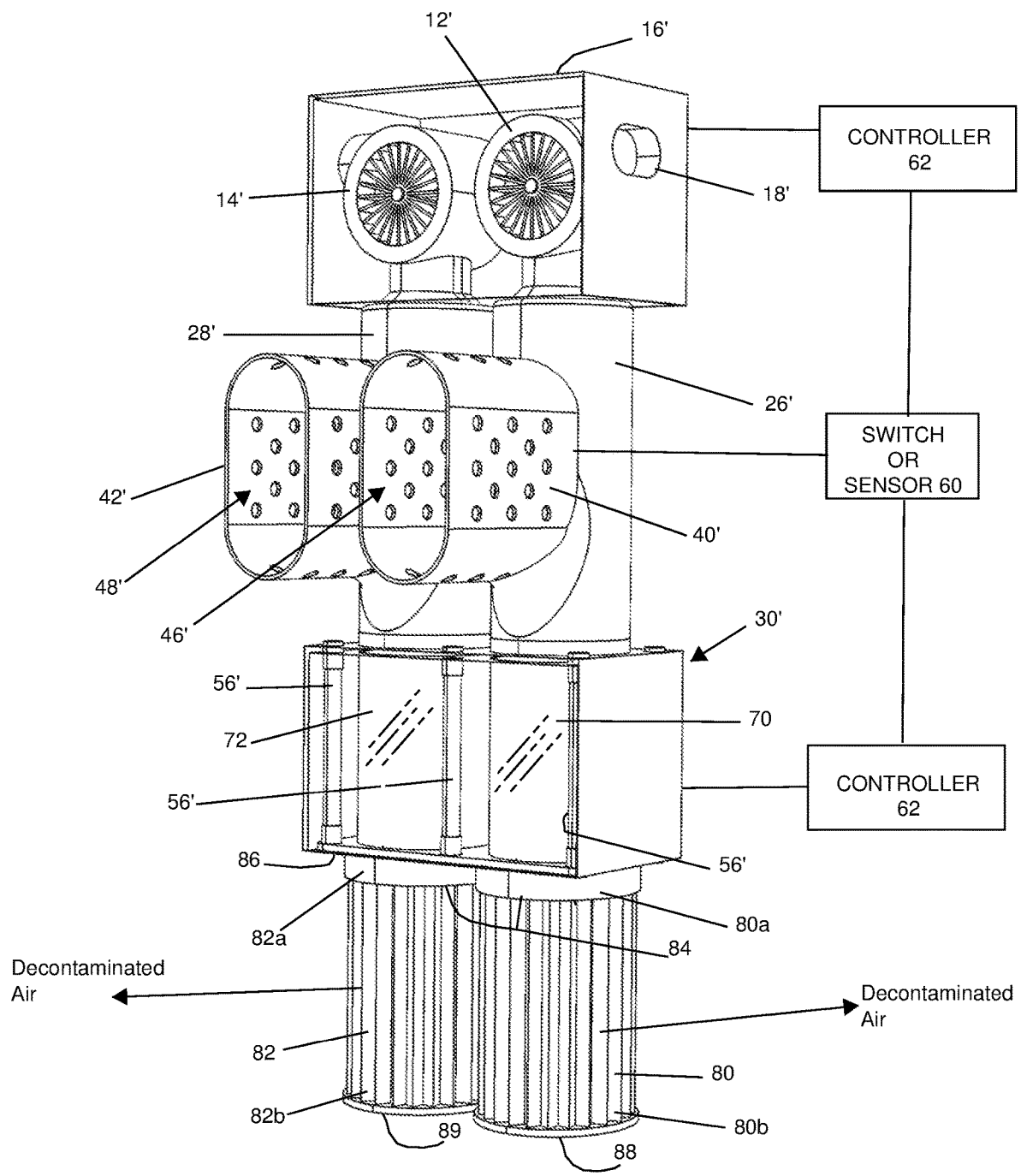
FIG. 8 is a view similar to FIG. 7 with FIGS. 7 and 8 illustrating the transparent tubular members that receive and permit passage of the waste air from the hand-receiving areas and an array of ultraviolet lights surrounding the transparent tubular members.
Figure 9:
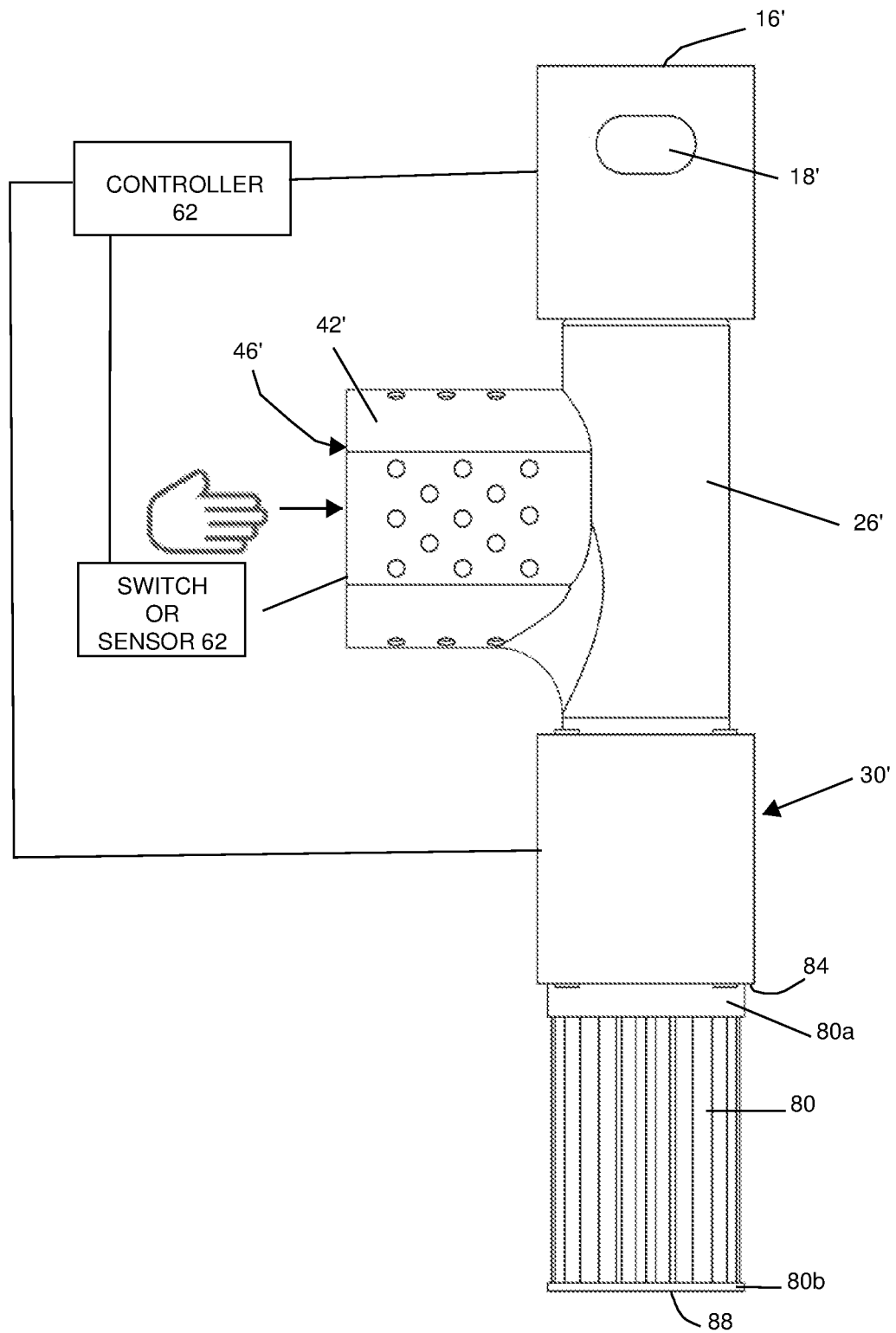
FIG. 9 is a right side view of the embodiment shown in FIG. 8.

As best illustrated in FIG. 3, note that each of the conduits 26 and 28 are generally tubular and define a high-volume air column dimensioned and sized to create a negative pressure in the openings 46 and 48 to facilitate drying a user's hands after they are positioned in the openings 46 and 48. In this regard, note that each of the conduits 26 and 28 comprises at least a portion that is dimensioned and sized to comprise a decreasing diameter or dimension which facilitates increasing air velocity and creating a negative air pressure in the openings 46 and 48 as the air flows through the conduits 26 and 28 and toward the at least one anti-bacterial treatment system 30. Note that each of the hand-receiving walls 42 and 44 are perforated to facilitate introducing ambient air from the surrounding environment to enter the hand-receiving openings 46 and 48, as best illustrated in FIG. 5. The flow of the air across the user's hands causes them to dry. After the air passes over the user's hands, it becomes "waste" air and enters the passageways 32 and 34 where it is joined by the airflow generated by the airflow generators 12 and 14 and ultimately is delivered to the at least one anti-bacterial treatment system 30, which will now be described. Thus, it should be understood that in this embodiment, the hand drying is performed by creating a negative pressure in the hand-receiving openings 46 and 48 defined by the hand-receiving walls 42 and 44, respectively.

The anti-bacterial treatment system 30 comprises at least one physical, biological or emissive means for removing, capturing and/or inactivating organic, inorganic or living matter from at least one of the airflow or the waste airflow after it has passed the user's hands. In the illustration being described, the at least one anti-bacterial treatment system 30 utilizes at least one filter and means for a irradiating the air as it passes through the anti-bacterial treatment system 30. In the illustration being described, the radiation means comprises at least one or a plurality of ultraviolet (UV) light sources 56 that may be energized to irradiate the airflow after it passes through the filters. Thus, after the air passes over the user's hands and enters either the first or second conduit 26 and 28, it enters the passageways 32 and 34, respectively, where it combines with the forced-air flow from the airflow generators 12 and 14, whereupon it is eventually delivered to the at least one anti-bacterial treatment system 30.

An optional exterior wall 50 may be provided to house the various components in the at least one anti-bacterial treatment system 30. It should be understood that the wall or bottom wall 30b may have one or more exhaust aperture or ports (not shown) to permit exhaust of the filtered and decontaminated air. The at least one anti-bacterial treatment system 30 comprises a top wall 30a and a bottom wall 30b and side walls 30c, 30d, 30e and 30f (FIGS. 1 and 4) which houses the components therein. In the illustration being described, the at least one anti-bacterial treatment system 30 comprises at least one or a plurality of filters, such as filters 52 and 54, for filtering the air received from the conduits 26 and 28, respectively. In this example, the air filters 52 and 54 are circular high-efficiency particulate air (HEPA) filters, but other filters such as carbon, ionic or UV light, to name a few, can be used. Air flows generally axially into the circular filters 52 and 54 and exits the filters 52 and 54 generally radially.

After filtration, the air is then subjected to ultraviolet radiation from the at least one or a plurality of ultraviolet (UV) light sources 56. Thereafter, the treated and decontaminated air is returned to the surrounding environment through the exhaust ports 61 and 63 (FIG. 1).

In this example, the at least one anti-bacterial treatment system 30 may be encapsulated and have at least one or a plurality of ducts for directing the decontaminated air into a duct system (not shown) which directs the decontaminated air to a desired location, such as the outside ambient environment. As mentioned earlier, the filters 52 and 54 are high-efficiency particulate air (HEPA) filters that are conventionally known.

It should be understood that in some embodiments described herein, the at least one anti-bacterial treatment system 30 is situated downstream of both the airflow generators 12 and 14 and the hand-receiving openings 46 and 48 so that at least a portion of the drying airflow or waste airflow, which is the airflow after it passes over a user's hands, combines with the positive airflow in either conduit 26 or 28 so that at least a portion of the drying airflow or waste airflow is filtered or treated to facilitate decontaminating the airflow. In this first embodiment, the hands of a user are placed in the vicinity of the negative pressure air intake by the user placing his or her hands in at least one of the hand-receiving openings 46 and 48 such that aerosols and air are drawn directly into the conduits 26 and 28, rather than the environment. It is important to understand that the negative pressure in the first and second hand-receiving openings 46 and 48 is created, at least in part, by a Venturi effect, where the high velocity air column of decreasing diameter is used to create the required negative air movement over the user's hands. In this regard, note that each conduit 26 and 28 comprise the frusto-conical shape or portion 26b and 28b, respectively, which increases fluid velocity and a resultant drop in pressure in or at the hand-receiving openings 46 and 48. Note that the inlet ends 26a and 28a of the conduits are in fluid communication with the airflow generators 12 and 14, respectively. As air flows into the frusto-conical portions 26b and 28b, a resultant increase in velocity of the airflow is caused, in turn, which causes a pressure drop or negative pressure in the hand-receiving openings 46 and 48. This, in turn, causes the Venturi effect mentioned earlier herein. It should be understood, however, that while the Venturi effect is preferred, the embodiments described are adapted to work without the frusto-conical portions 26b and 28b.

During operation, after the user has washed his or her hands or treated them with a fluid, the user approaches the hand dryer 10 and places his or her hands in or in proximity to the hand-receiving openings 46 and 48. A switch or sensor 60 (FIG. 1), such as an infra-red sensor, senses the user's hands approaching the hand-receiving openings 46 and 48, whereupon it generates a sense signal that is received by a controller 62. The controller 62 energizes the airflow generators 12 and 14 and the at least one or plurality of ultraviolet light sources 56 in response, thereby causing the user's hands to be dried while substantially simultaneously decontaminating the airflow passing through the hand dryer 10.

FIGS. 6-9 show another embodiment of the invention. In this embodiment, like parts are identified with the same part numbers, except a prime mark ("'") has been added to the part numbers in FIGS. 6-9. In the embodiment being described, one or more features of the air purifiers shown in the following U.S. Patents, which are owned by the Assignee of the present application, all of which are incorporated herein by reference and made a part hereof, may be used or adapted for use in the forced-air hand dryer 10: U.S. Pat. Nos. 9,433,693; 9,457,119; 9,764,054; 10,039,854 and U.S. Patent Publication Nos. 2016/0263267; 2018/0133084 and 2018/0133355.

In this embodiment, at least one anti-bacterial treatment system 30' comprises the housing 16' and a first transparent tubular member 70 and second transparent tubular member 72 conventionally mounted in the housing 16'. The transparent tubular members 70 and 72 may be glass or made from a polymer and define passageways that are in fluid communication with the passageways 32' and 34' of the first conduit 26' and second conduit 28', respectively. Notice the at least one or a plurality of ultraviolet (UV) light sources 56' are situated in an array around the tubular members 70 and 72 and adapted to irradiate the airflow as it travels though the tubular members 70 and 72, respectively. The transparent tubular members 70 and 72 are in fluid communication with a first filter 80 and second filter 82, respectively. The first filter 80 has a first end 80a (FIG. 8) and the second filter 82 has a second end 82a that are affixed to a filter support 84, which in turn is conventionally mounted to a bottom surface 86 of the housing 16' as illustrated. The filters 80 and 82 have ends 80b and 82b that are closed by planar members 88 and 89 (FIG. 8), respectively.

For ease of understanding, FIG. 8A illustrates the transparent tubular members 70, 72 and their associated filters 80, 82. In the illustration being described, each of the transparent tubular members 70, 72 comprise a bottom 71 that has a female guide 87 in the form of a plurality of mating apertures 87a. Note that each of the filters 80, 82 comprise a collar 91 and a male guide 93 having a plurality of elongated, generally circular and hollow projections 95. The projections 95 mate with and are received in the plurality of mating apertures 87a of the female guide 87. The transparent tubular members 70, 72, which may be glass, plexiglass, plastic, polymer or other materials are situated on the filters 80, 82 and the end 71 is received in the area 97 between the collar 91 and the male guide 93.

When the user inserts his or her hands into the hand-receiving openings 46' and 48', sensor 60' senses them and a signal is sent to controller 62' which activates the first and second airflow generators 12' and 14' and the ultraviolet light sources 56'. This causes the airflow, in the manner described earlier herein relative to the embodiment of FIGS. 1-5, which causes a negative pressure in the hand-receiving openings 46' and 48'. Thereafter, the waste airflow and airflow generated by the first and second airflow generators 12' and 14' passes through the transparent tubular members 70 and 72, whereupon they are exposed to the ultraviolet radiation from the ultraviolet light sources 56' which were also activated by the controller 62. Thereafter, the airflow passes through the filters 80 and 82, which further decontaminates the airflow, as with the embodiment described earlier herein.

The filter and irradiation means are located serially relative to each other in this embodiment, but they could be arranged in a different order. For example, note that in the first embodiment of FIG. 2, the airflow first passes through the filters 52 and 54 before it is subjected to radiation from the ultraviolet light sources 56.

As mentioned earlier, one or more features of the patents referenced earlier herein may be incorporated and used with one of more of the embodiments described herein. In this regard, one or more bafflers or airflow interrupters may be placed inside the transparent tubular members 70 and 72 to interrupt the airflow so that it is subjected to the UV radiation longer. For example, one or more small tubular members or quartz members may be situated in the transparent tubular members 70 and 72. Thus, the transparent tubular members 70 and 72 may be hollow, but alternatively, they could be filled with reflective, focusing, concentrating or baffling apparatus or airflow interrupter to slow or create turbulence within the airflow passing through the passageways 32' and 34' in order to improve the ultraviolet effectiveness. For example, features of the system and devices of U.S. Pat. No. 9,457,119 issued Oct. 4, 2016, may be used. This patent is owned by the same Assignee as the present application and is incorporated herein by reference and made a part hereof as mentioned earlier. Again, such features may include providing at least one baffle or airflow interrupter, such as the at least one baffle or airflow interrupter that may comprise a plurality of tubular quartz members (not shown) that are situated in the passageways 32 and 34.

During operation, the air flows into the transparent tubular members 70 and 72, where it is subjected to the ultraviolet radiation generated by the ultraviolet light sources 56'. Thereafter, the air flows into the filters 80 and 82, whereupon the air is further decontaminated and, ultimately, exhausted to the environment or other desired location.

Figure 10:
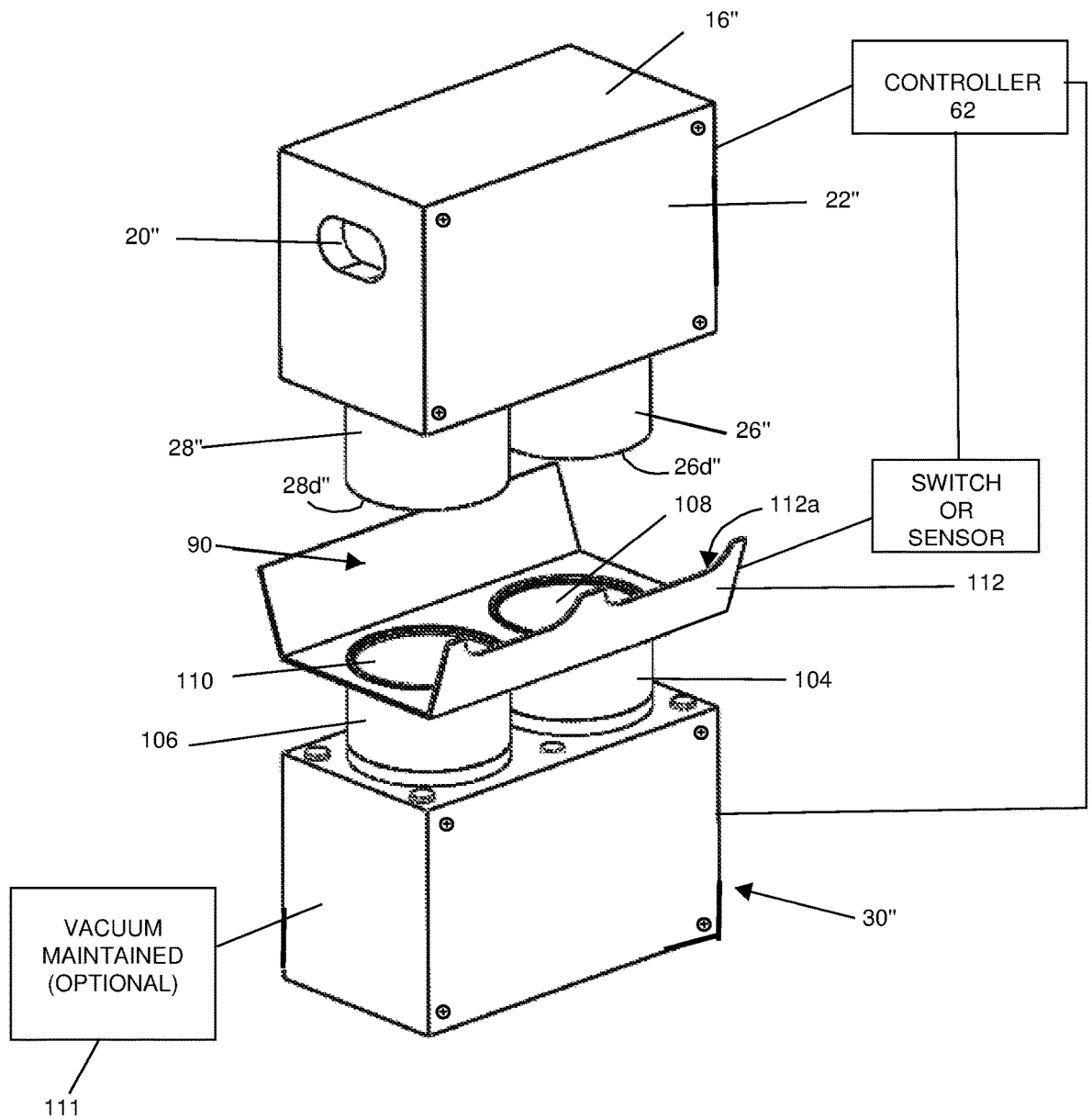
FIG. 10 is a perspective view showing a forced-air hand dryer that creates a positive pressure at a hand-receiving area.
Figure 11:
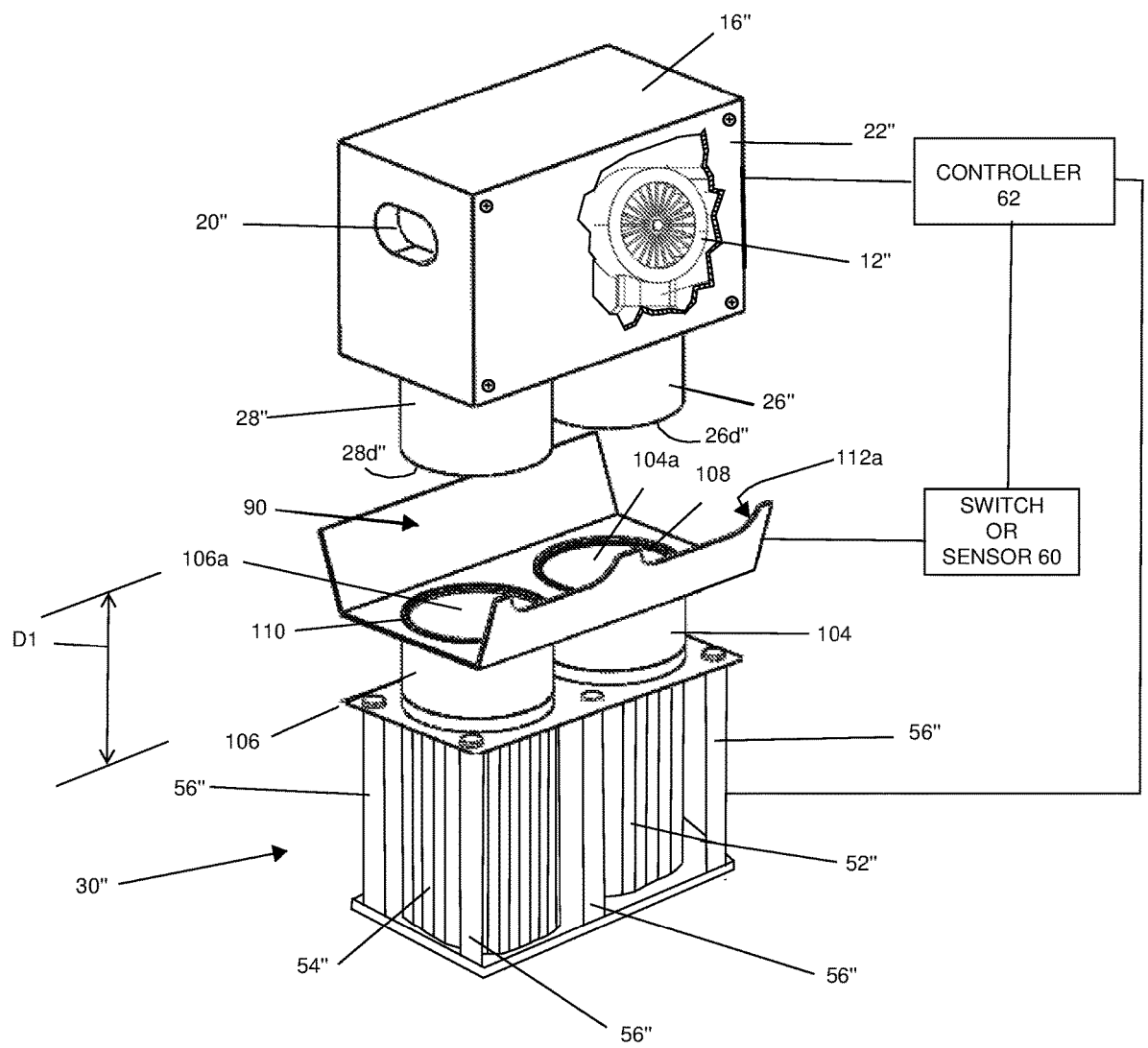
FIG. 11 is another view of the embodiment shown in FIG. 10 illustrating details of the decontamination system.

FIGS. 10 and 11 illustrate still another embodiment of a forced-air hand dryer. In this embodiment, like parts are identified with the same part numbers except that the double prime mark ("" ") is added to the part numbers of the embodiments of FIGS. 10 and 11.

In this embodiment, note that the conduits 26" and 28" are interrupted and comprise generally a constant dimension and diameter and have outlets 26d" and 28d", respectively, that deliver forced air to a hand-drying area 90. The forced air is generated by at least one or a plurality of airflow generators 12" and 14" which receive incoming air from an inlet 20". A waste air capturing means is coupled to a second pair of conduits 104 and 106 and means or apparatus having at least a portion that defines a surface or generally U-shaped wall 112 for channeling or funneling the forced air from the area 90 and into the conduits 104 and 106, which in the illustration being described are generally tubular and circular and define passageways 108 and 110, respectively, for receiving the forced air from the area 90.

The wall 112 may comprise at least one or a plurality of notched out areas 112a (FIG. 10) to assist or guide the user in placing his or her hands in the hand-drying area 90. The wall 112 is coupled to the inlet ends 104a and 106a as illustrated. A distance D1 (FIG. 11) is selected and sized to be large enough to permit a user to insert hands into the area 90, but also small enough so that all or substantially all of the forced air from the airflow generators 12" and 14" can be captured in the collection area or chamber defined by the at least one anti-bacterial treatment system 30". Thereafter, it is treated in substantially the same manner as described earlier herein relative to the embodiment of FIGS. 1-5.

It should be understood that the high pressure air generation system creates a positive pressure at the area 90 and the at least one anti-bacterial treatment system 30" provides a separate negative pressure collector. In this regard, one or more separate air or vacuum generators 111 (FIG. 10) could be provided in the at least one anti-bacterial treatment system 30 in order to facilitate generating negative air pressure at the inlets 104a and 106a of the passageways 108 and 110, respectively, thereby further facilitating the capturing of the forced air of the airflow generators 12" and 14" downstream of the hand-drying area 90.

In operation, the user places his or her hands in the hand-drying area 90, whereupon the sensor 60 senses such presence and the controller 62 energizes the at least one or the plurality of airflow generators 12" and 14" and the ultraviolet light sources 56". If the optional vacuum generators 111 are included, they are also caused to be turned on by controller 62 as well in order to create a negative pressure at the inlets 104a and 106a of conduits 104 and 106, respectively, in the at least one anti-bacterial treatment system 30". As the user places his or her hands in the hand drying area 90, air flow generated by the at least one or plurality of airflow generators 12" and 14" forces the air movement over the hands of the user and waste air and aerosol is ejected from the user's hands and is collected in the at least one anti-bacterial treatment system 30", thereby reducing or preventing aerosols, bacteria and unwanted contaminants from entering the surrounding environment. The airflow is filtered in substantially the same manner as with the first embodiment described earlier herein.

Referring now to FIGS. 12-15, still another embodiment is shown. In this embodiment, like parts are identified with the same part numbers, except that a triple prime mark ("'''") has been added to the part numbers of this embodiment. This embodiment is similar to the embodiment shown and described earlier relative to FIGS. 6-9. In this embodiment, however, the conduits 26''' and 28''' are tubular and generally cylindrical and define inlets that are open to atmosphere. Rather than the at least one or a plurality of airflow generators 12''' and 14''' or vacuum fans being situated in proximity to the inlet ends 26a''' and 28a''', the airflow generators 12''' and 14''' or vacuum fans are situated downstream of the at least one anti-bacterial treatment system 30''' and pull air through the hand dryer 10'''. In this embodiment, the airflow generators or vacuum fans 12''' and 14''' create negative pressure in the hand-receiving openings 46''' and 48'''. In this regard, the airflow generators or vacuum fans 12''' and 14''' generate the negative pressure in the hand-receiving openings 46''' and 48''' by generating a vacuum flow or airflow that exhausts through the opening or outlet ducts 20''' in the wall 112.

Figure 14:
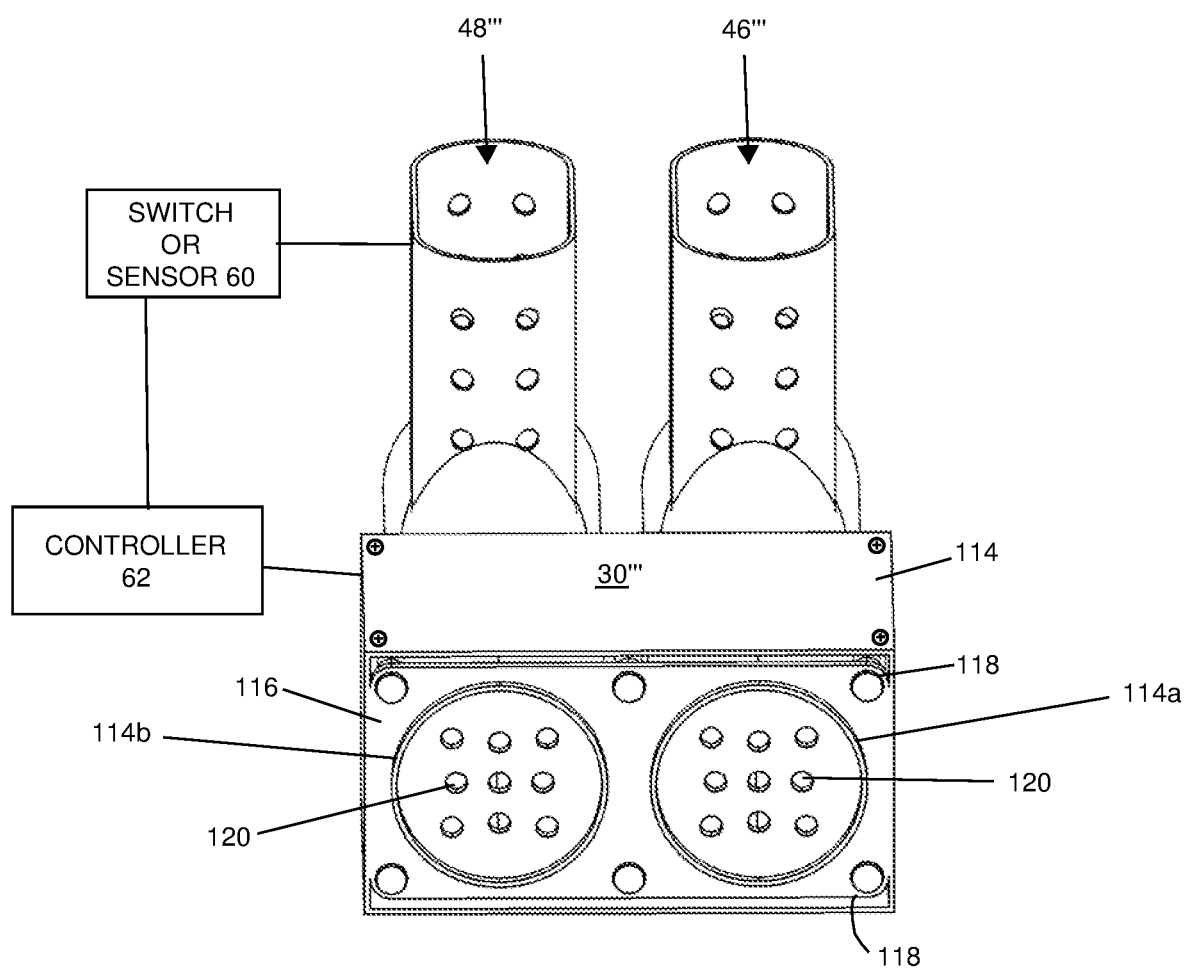
FIG. 14 is a view of a portion of the embodiment shown in FIG. 13 illustrating a bottom surface with apertures for permitting airflow from the at least one anti-bacterial decontamination system to at least one or a plurality of airflow generators.
Figure 15:
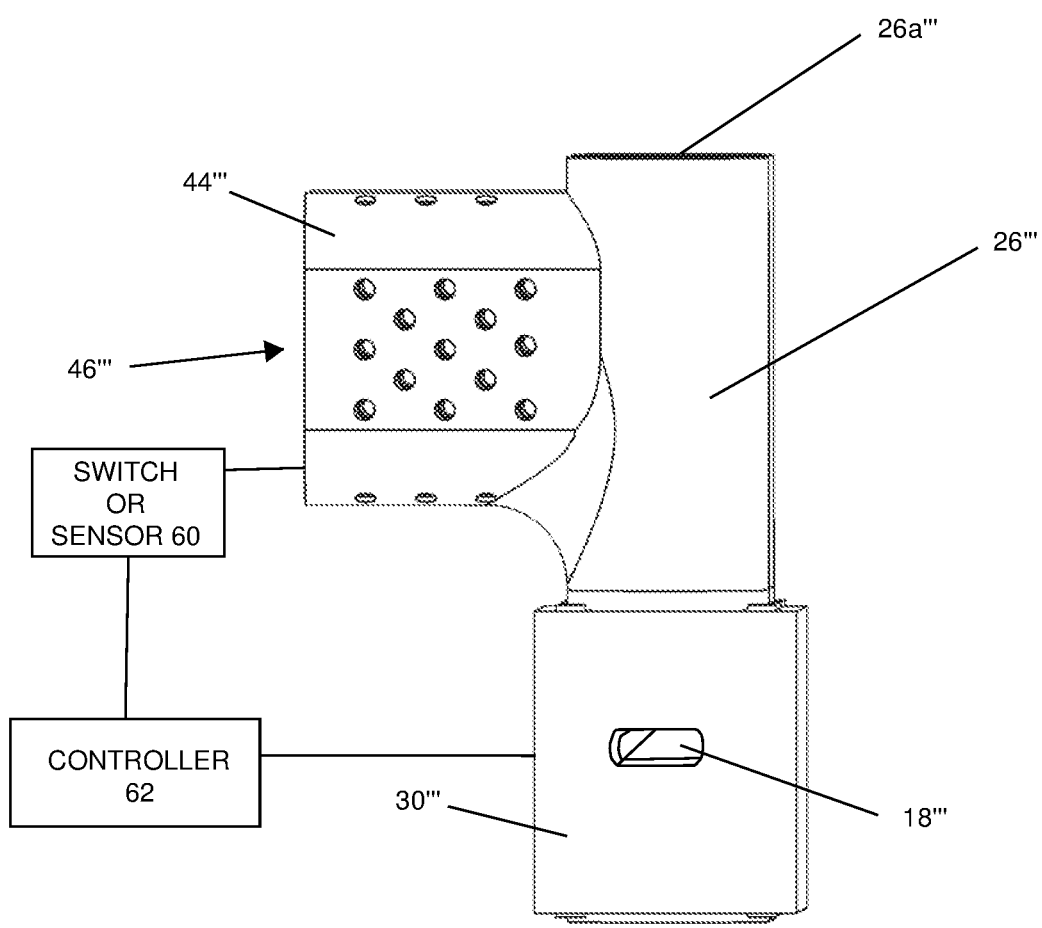
FIG. 15 is a side view of the portion of the hand dryer shown in FIG. 14.

The at least one anti-bacterial treatment system 30''' comprises the housing 114 (FIG. 14) that encases and houses the tubular members 70''' and 72''' and ultraviolet light sources 56''' as illustrated. The housing 114 comprises a bottom 116, which may be integral, monolithically formed, fastened or adhered to the housing 114 as illustrated in FIG. 14. A plurality of slots 118 and apertures 120 are provided in at least one surface to permit the airflow to flow from the at least one anti-bacterial treatment system 30''' to the airflow generators 12''' and 14''' as shown. The inlet ends of the airflow generators 12''' and 14''' or vacuum fans pull air through the first transparent tubular member 70''' and second transparent tubular member 72''' while UV light from the UV light sources 56''' further decontaminate the air.

Figure 12:
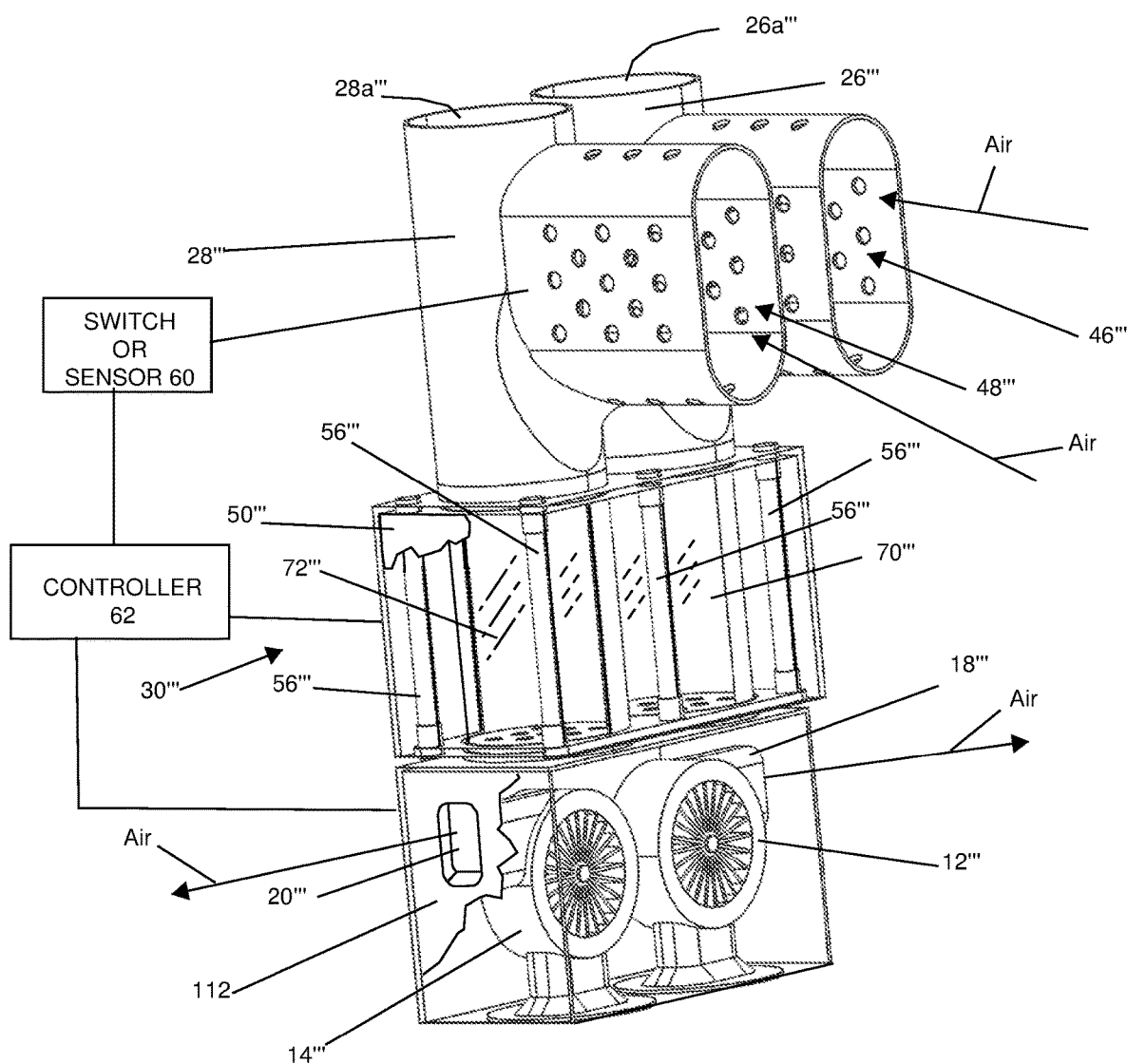
FIG. 12 is another embodiment that creates a negative pressure at the at least one or a plurality of hand-receiving areas and illustrating the at least one or a plurality of airflow generators being situated downstream of the hand-receiving areas.
Figure 13:
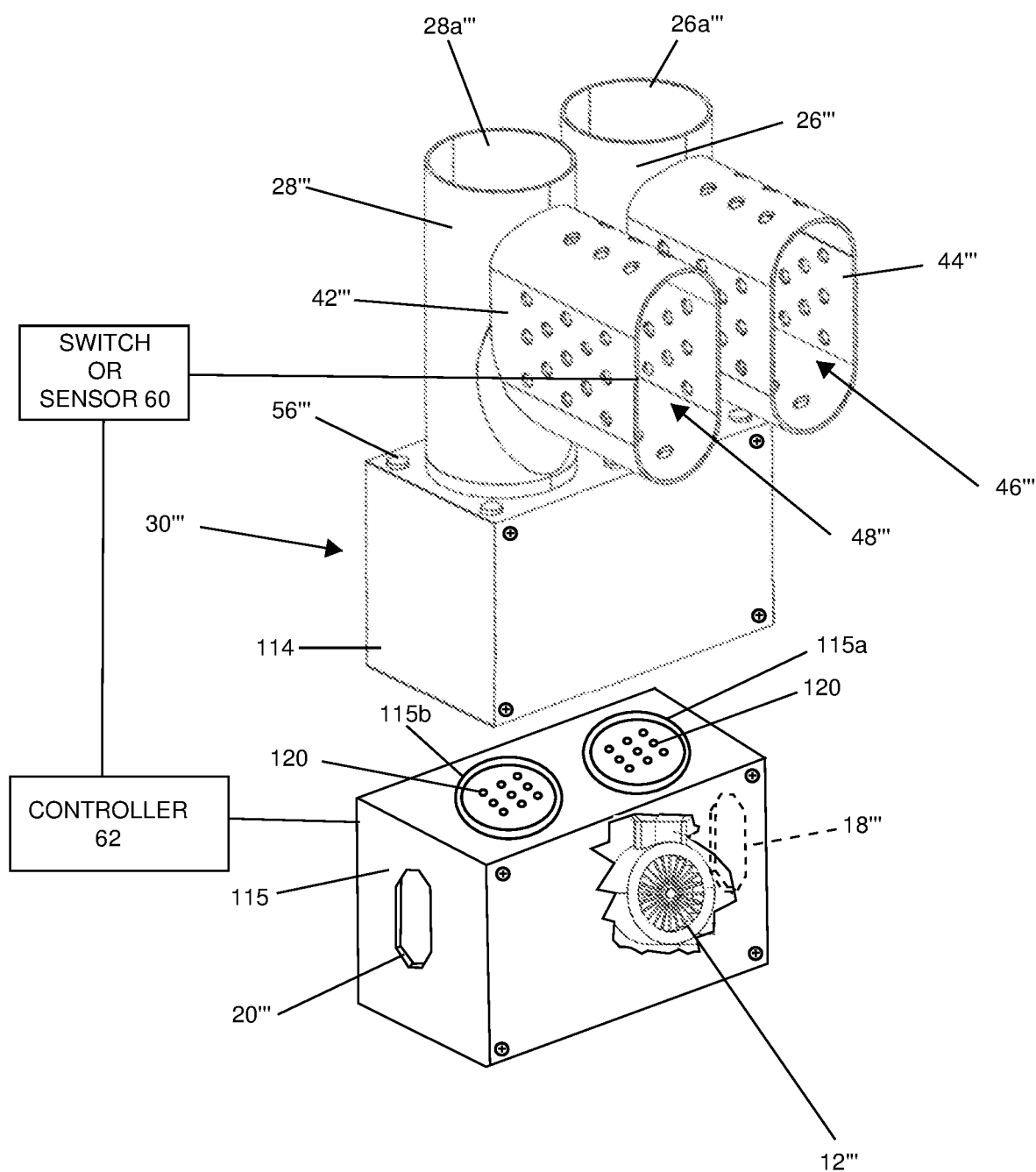
FIG. 13 is partial fragmentary view illustrating various features of the embodiment shown in FIG. 12.

Accordingly, when these fans are energized, they cause a vacuum or suction to pull air from the atmosphere into the inlet ends 26a''' and 28a''' and from the first and second hand-receiving openings 46''' and 48''' such that the air is sucked or vacuumed through the transparent tubular members 70''' and 72''', whereupon the first and second airflow generators 12''' and 14''' force the air through the outlet ducts 18''' and 20''' (FIG. 12).

Note that the housing 114 has the bottom 116 and a plurality of integral circular walls 114a and 114b. The air generator housing 115 has circular walls 115a and 115b that are sized and adapted to receive and mate with the walls 114a and 114b and provide a guide or reminder for facilitating mounting the housing 114 of the decontamination system 30''' onto the air generator housing 115 so that the tubular members 70''' and 72''' become aligned with and on the air generator housing 115.

As with the prior embodiments, as air is forced and pulled through the at least one anti-bacterial treatment system 30''', the waste air becomes filtered and decontaminated by being exposed to filtration and/or ultraviolet decontamination and then exhausted to the environment or other desired location.

As mentioned earlier herein, while the embodiments described show both filtration and ultraviolet decontamination or radiation, it should be understood that other means for decontamination could be provided, and more or fewer decontamination means may be used. For example, it may be desirable just to provide filtration in some applications or, alternatively, ultraviolet decontamination in other applications. In the embodiments being described, maximum decontamination is desired so both filtration and decontamination are shown, but again, other filtering and decontamination means or stages may be added or fewer filtering and decontamination means may be used.

ADDITIONAL CONSIDERATIONS

1. Note that the embodiment shown in FIGS. 1-5, show a plurality of conduits 26 and 28 and airflow generators 12 and 14, but a single conduit and single airflow generator could be provided. Alternatively, more conduits or airflow generators may be used.

2. It should be understood that the at least one anti-bacterial treatment system 30 shows a plurality of filters 52 and 54, but the waste air from the at least one or a plurality of conduits, such as conduits 26 and 28, could be directed to a single filter surrounded by a plurality of ultraviolet light sources 56. Alternatively, more filters may be used.

3. Although the embodiment shows a plurality of hand-receiving walls 42 and 44 that define the hand-receiving openings 46 and 48, respectively, a single hand-receiving area could be provided so that the user may place his or her hands directly in a single opening.

4. It should be understood that the hand dryer 10 of the embodiments being described may be used in any appropriate environment where a user needs to dry his or her hands. This could be a hospital environment, a lavatory or bathroom environment, a kitchen or cooking environment, school, public restrooms, a surgical room or hospital environment, elderly home, or other healthcare of food-service environments.

5. It should be understood that the decontamination system for each embodiment comprises at least one physical, biological or emissive means for removing, capturing and/or inactivating organic, inorganic or living matter from at least one of the airflow or the drying airflow. Advantageously, the embodiment being described herein reduces or eliminates the potential for environmental contamination by decontaminating the airflow generated by and passing into and through the hand dryer 10.

6. Each of the embodiments refers to at least one airflow generator which, in the illustration being described, can be a fan, such as at least one radial fan of the type illustrated and shown and which are conventionally shown.

7. The hand dryer 10 and components of the system 30 are all sourced and available from Aerobiotix, Inc., 350 Fame Road, West Carrollton, Ohio 45449.

8. It should be understood that the hand dryer may be mounted to a wall, frame or other environment where it is to be situated. It may also be mounted on a movable cart or may be provided with wheels (not shown) so that the forced-air hand dryer 10 is movable and portable.

9. It should be understood that one or more side walls or panels of the housing 16 of the airflow generators 12 and 14 may be detachable and removable for service as well as one or more of the walls or panels making up the housing of the at least one anti-bacterial decontamination system 30.

9. It should be understood that the system 30 can be exhausted into an HVAC return duct or a central system.

Advantageously, the embodiments shown and described herein could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A hand dryer comprising:
    at least one airflow generator for generating a primary airflow for said hand dryer;
    at least one decontamination system;
    at least one conduit for defining at least one passageway for fluidly coupling said at least one airflow generator to said at least one decontamination system so that air can flow therebetween;
    at least one hand-receiving opening that is in fluid communication with said at least one passageway and dimensioned to receive at least one hand of a person, said at least one airflow generator causing a drying airflow in said at least one hand-receiving opening when said primary airflow passes said at least one hand-receiving opening;
    said at least one airflow generator generating said primary airflow that causes said drying airflow across said at least one hand of said person to facilitate drying said at least one hand after it has been positioned in said at least one hand-receiving opening;
    wherein after said drying airflow passes said at least one hand, said drying airflow becomes waste airflow that combines with said primary airflow to provide a combined airflow;
    said at least one decontamination system being situated downstream of said at least one hand-receiving opening so that at least a portion of said at least one of said drying airflow, said primary airflow, said waste airflow or said combined airflow is channeled by said at least one conduit to said at least one decontamination system so that at least a portion of said drying airflow, said waste airflow, said primary airflow, or said combined airflow is filtered or treated to facilitate reducing contamination downstream of where said waste air combines with said primary airflow to provide said airflow.

2. The hand dryer as recited in claim 1 wherein said drying airflow is caused by a negative pressure at said at least one hand-receiving opening.

3. The hand dryer as recited in claim 1 wherein said drying airflow is caused by a positive pressure at said at least one hand-receiving opening.

4. The hand dryer as recited in claim 1 wherein said at least one conduit comprises at least one tubular member that defines a high velocity air column dimensioned and sized to create a negative pressure at said at least one hand-receiving opening.

5. The hand dryer as recited in claim 4 wherein said at least one tubular member comprises a generally decreasing dimension in order to facilitate a Venturi effect to create a negative pressure at said at least one hand-receiving opening.

6. The hand dryer as recited in claim 4 wherein said tubular member is dimensioned to create a Venturi effect that causes a negative pressure at said at least one hand-receiving opening.

7. The hand dryer as recited in claim 1 wherein said at least one decontamination system comprises at least one physical, biological or emissive system for removing, capturing and/or inactivating organic, inorganic or living matter from at least one of said airflow or said drying airflow.

8. The hand dryer as recited in claim 7 wherein said at least one decontamination system comprises at least one of filter or ultraviolet light source for generating ultraviolet light for decontaminating the air received by said at least one decontamination system.

9. The hand dryer as recited in claim 1 wherein said hand dryer comprises a plurality of conduits defining a plurality of passageways, respectively, for directing airflow from said at least one airflow generator to said at least one decontamination system.

10. The hand dryer as recited in claim 9 wherein said hand dryer comprises a plurality of hand-receiving openings in fluid communication with said plurality of passageways, each of said plurality of hand-receiving openings being situated adjacent each other so that the person may situate at least one hand in each of said plurality of hand-receiving openings.

11. The hand dryer as recited in claim 10 wherein each of said plurality of hand-receiving openings are defined by at least one wall having a plurality of perforations therein for facilitating creation of said drying airflow.

12. The hand dryer as recited in claim 9 wherein said hand dryer comprises a plurality of fans for creating an airflow in each of said plurality of conduits, respectively.

13. The hand dryer as recited in claim 12 wherein said at least one decontamination system comprises at least one filter or ultraviolet light source associated with an outlet end of each of said plurality of conduits.

14. The hand dryer as recited in claim 1 wherein said at least one airflow generator is a fan.

15. The hand dryer as recited in claim 1 wherein said drying airflow is caused by a negative pressure at said at least one hand-opening.

16. A hand dryer comprising:
    at least one airflow generator for generating a primary airflow for drying a user's hands;
    at least one hand-drying area operatively associated with said at least one airflow generator for defining a place for said user to place at least one of said user's hands; and
    a decontamination system downstream of said hand-drying area for receiving waste airflow after it passes at least one said user's hands;
    said at least one airflow generator generating a positive airflow over the user's hands to facilitate drying them and said decontamination system receiving said waste airflow and decontaminating said waste airflow after it has passed over the user's hands;

at least one conduit for defining at least one passageway for fluidly coupling said at least one airflow generator to said decontamination system so that air can flow therebetween;

said at least one hand-drying area being in fluid communication with said at least one passageway and dimensioned to receive said at least one hand, said at least one airflow generator causing a negative pressure and a drying airflow in said at least one hand-drying area when said primary airflow passes said at least one hand-drying area;

said at least one airflow generator generating said primary airflow that causes said negative pressure and said drying airflow across said at least one hand to facilitate drying said at least one hand after it has been positioned in said at least one hand-drying area;

wherein after said drying airflow passes said at least one hand, said drying airflow becomes waste airflow that combines with said primary airflow to provide a combined airflow;

said decontamination system being situated downstream of said at least one hand-drying area so that at least a portion of said at least one of said drying airflow, said primary airflow, said water airflow, or said combined airflow is channeled by said at least one conduit to said decontamination system so that a t least a portion of said drying airflow, said waste airflow, said primary airflow, or said combined airflow is filtered or treated by said decontamination system to facilitate reducing contamination downstream of where said waste air combines with said primary airflow to provide said combined airflow.

17. The hand dryer as recited in claim 16 wherein said decontamination system comprises an input, said input having at least a portion that defines a surface for channeling or funneling air into said decontamination system.

18. The hand dryer as recited in claim 16 wherein said at least one airflow generator comprises an outlet and said decontamination system comprises an inlet, said outlet and inlet being spaced from each other and said hand-drying area being situated between said outlet and said inlet; said outlet having a predetermined configuration adapted to direct airflow from said at least one airflow generator to said hand-drying area and said inlet of said decontamination system having a predetermined configuration that facilitates channeling or funneling air into said decontamination system after it has passed said user's hands.

19. The hand dryer as recited in claim 16 wherein said drying airflow is caused by a positive pressure at said hand-drying area.

20. The hand dryer as recited in claim 16 wherein said decontamination system comprises at least one physical, biological or emissive system for removing, capturing and/or inactivating organic, inorganic or living matter from at least one of said airflow or said drying airflow.

21. The hand dryer as recited in claim 20 wherein said decontamination system comprises at least one of either an air filter or an ultraviolet light source for generating ultraviolet light for decontaminating the air received by said decontamination system.

22. The hand dryer as recited in claim 21 wherein said decontamination system comprises at least one filter or ultraviolet light source downstream of an inlet to said decontamination system.

23. The hand dryer as recited in claim 16 wherein said at least one airflow generator is at least one radial fan.

24. The hand dryer as recited in claim 16 wherein said at least one airflow generator generates a positive pressure drying airflow at said hand-drying area.

25. The hand dryer as recited in claim 16 wherein said decontamination system comprises a negative pressure collector for generating a negative pressure relative to said hand-drying area to facilitate preventing aerosols or said waste air from entering a surrounding environment.

26. The hand dryer as recited in claim 25 wherein said negative pressure collector comprises a vacuum generator for generating said negative pressure at an inlet of said decontamination system.

27. A hand dryer comprising:
at least one airflow generator for generating a primary airflow;
at least one hand-receiving area defining at least one hand-receiving opening for a user to place at least one hand; and
at least one decontamination system downstream of said at least one hand-receiving area;
said at least one airflow generator generating a negative pressure at said hand-receiving area to cause a drying airflow across said at least one hand of said user to faciliate drying said at least one hand after it has been positioned in said at least one hand-receiving area; and
at least one conduit for defining at least one passageway for fluidly coupling said at least one airflow generator to said at least one decontamination system so that air can flow therebetween;
said at least one hand-receiving area being in fluid communication with said at least one passageway and dimensioned to receive said at least one hand, said at least one airflow generator causing a drying airflow in said at least one hand-receiving area when said primary airflow passes said at least one hand-receiving area;
said at least one airflow generator generating said primary airflow that causes said drying airflow across said at least one hand to facilitate drying said at least one hand after it has been positioned in said at least one hand-receiving area;
wherein after said drying airflow passes said at least one hand, said drying airflow becomes waste airflow that combines with said primary airflow to provide a combined airflow;
said at least one decontamination system being situated downstream of said at least one hand-receiving area so that at least a portion of said at least one of said drying airflow, said waste airflow, said primary airflow, or said combined airflow is channeled by said at least one conduit to said at least one decontamination system so that a t least a portion of said drying airflow, said waste airflow, said primary airflow, or said combined airflow is filtered or treated by said at least one decontamination system to facilitate reducing contamination downstream of where said waste air combines with said primary airflow to provide said combined airflow.

28. The hand dryer as recited in claim 27 wherein after said airflow passes at least one of said user's hands, at least a portion of said airflow is received or channeled into said at least one decontamination system as a result of a negative pressure in said at least one hand-receiving area is generated by said at least one airflow generator so that at least a portion of said airflow is filtered or treated to facilitate reducing contamination.

29. The hand dryer as recited in claim 27 wherein said at least one airflow generator is located downstream of said hand-receiving area.

30. The hand dryer as recited in claim 29 wherein said at least one airflow generator is located in said at least one decontamination system.

31. The hand dryer as recited in claim 27 wherein said drying airflow is caused by a negative pressure at said at least one hand-receiving area.

32. The hand dryer as recited in claim 27 wherein said hand dryer comprises at least one conduit for receiving and channeling ambient air toward said hand-receiving area, said at least one conduit comprising at least one hand enclosure, respectively, for receiving said at least one hand of the user.

33. The hand dryer as recited in claim 32 wherein said at least one hand enclosure is perforated to permit ambient air to enter into said at least one hand-receiving area.

34. The hand dryer as recited in claim 27 wherein said at least one decontamination system comprises at least one physical, biological or emissive system for removing, capturing and/or inactivating organic, inorganic or living matter from at least one of said drying airflow, said waste airflow, said primary airflow or said combined airflow.

35. The hand dryer as recited in claim 34 wherein said at least one decontamination system comprises at least one of an air filter or ultraviolet light source for generating ultraviolet light for decontaminating said drying airflow, said waste airflow, said primary airflow or said combined airflow received by said at least one decontamination system.

36. The hand dryer as recited in claim 27 wherein said hand dryer comprises a plurality of conduits defining a plurality of passageways, respectively, for directing airflow from said at least one airflow generator to said at least one decontamination system.

37. The hand dryer as recited in claim 36 wherein said hand dryer has at least one first hand-receiving opening and at least one second hand-receiving opening, both of which are in fluid communication with said plurality of passageways so that said user may situate at least one hand in at least one of said first and second hand-receiving openings, said first and second hand-receiving openings being side-by-side.

38. The hand dryer as recited in claim 37 wherein each of said plurality of hand-receiving openings are defined by at least one wall having a plurality of perforations therein for facilitating creation of said drying airflow.

39. The hand dryer as recited in claim 36 wherein said hand dryer comprises a plurality of fans situated in said at least one decontamination system for creating a negative air pressure at said at least one hand-receiving area.

40. The hand dryer as recited in claim 36 wherein said at least one decontamination system comprises at least one of either a filter or an ultraviolet light source associated with an outlet end of each of said plurality of conduits.

41. The hand dryer as recited in claim 27 wherein said at least one airflow generator is a fan associated with said at least one decontamination system.

42. The hand dryer as recited in claim 27 wherein said at least one decontamination system comprises at least one physical, biological or emissive system for removing, capturing and/or inactivating organic, inorganic or living matter from at least one of said waste airflow, said combined airflow, said primary airflow or said drying airflow.

* * * * *